(12) United States Patent
Garoff et al.

(10) Patent No.: US 6,420,499 B1
(45) Date of Patent: Jul. 16, 2002

(54) CATALYST COMPONENT COMPRISING MAGNESIUM, TITANIUM, A HALOGEN AND AN ELECTION DONOR, ITS PREPARATION AND USE

(75) Inventors: Thomas Garoff, Helsinki; Timo Leinonen, Tolkkinen; Sirpa Ala-Huikku, Helsinki, all of (FI)

(73) Assignee: Borealis Technology Oy, Porvoo (FI)

( * ) Notice: Subject to any disclaimer, the term of this patent is extended or adjusted under 35 U.S.C. 154(b) by 0 days.

(21) Appl. No.: 09/216,882

(22) Filed: Dec. 21, 1998

(30) Foreign Application Priority Data

Dec. 23, 1997 (FI) .................................................. 974621
Dec. 23, 1997 (FI) .................................................. 974622

(51) Int. Cl.$^7$ .............................. C08F 4/50; C08F 4/52; B01J 31/00
(52) U.S. Cl. ...................... 526/123.1; 526/90; 526/126; 526/127; 526/129; 526/348; 526/351; 502/103; 502/118; 502/125; 502/128
(58) Field of Search ................................. 502/103, 118, 502/125, 128; 526/90, 123.1, 126, 348, 351, 127, 129

(56) References Cited

U.S. PATENT DOCUMENTS

| | | | |
|---|---|---|---|
| 4,308,170 A | * 12/1981 | Mizogami et al. | ....... 252/429 B |
| 4,727,051 A | 2/1988 | Breen | ................... 502/126 |
| 4,784,983 A | * 11/1988 | Mao et al. | ................... 502/111 |
| 5,130,284 A | * 7/1992 | Terano et al. | ............... 502/125 |
| 5,488,022 A | * 1/1996 | Takahashi et al. | ........... 502/115 |

FOREIGN PATENT DOCUMENTS

| | | |
|---|---|---|
| EP | 0171200 A2 | 2/1986 |
| EP | 0195497 A2 | 9/1986 |
| EP | 0217843 | 6/1988 |
| EP | 0288762 A2 | 11/1988 |
| EP | 0297076 A2 | 12/1988 |
| EP | 491566 B1 | 6/1992 |
| EP | 0526941 A1 | 2/1993 |
| EP | 0743326 A1 | 11/1996 |
| EP | 748820 A1 | 12/1996 |
| FI | 92837 | 9/1994 |
| FI | 99247 | 9/1997 |
| WO | 91 05608 | 5/1991 |

* cited by examiner

Primary Examiner—Elizabeth D. Wood
(74) Attorney, Agent, or Firm—Birch, Stewart, Kolasch & Birch, LLP

(57) ABSTRACT

The invention relates to a novel process for the preparation of an olefin polymerization catalyst component comprising magnesium, titanium, a halogen and an electron donor. The process comprises the steps of:

(i) reacting a titaniumless magnesium compound (a) containing an alkoxy moiety, which titaniumless magnesium compound is selected from the group consisting of a compound or complex containing halogen and alkoxy linked to magnesium, a complex containing a magnesium dihalide and an alcohol, and a non-complex magnesium dialkoxide, with a halogen compound (b) being capable of forming the electron donor by replacement of its halogen by said alkoxy moiety, to give an intermediate (ab), and (ii) reacting said intermediate (ab) with a titanium halide (c), or (i)' reacting a titaniumless magnesium compound (a) containing an alkoxy moiety, which titaniumless magnesium compound is selected from the group consisting of a compound or complex containing halogen and alkoxy linked to magnesium, and a complex containing a magnesium dihalide and an alcohol, with a titanium halide (c), to give an intermediate (ac), and (ii)' reacting said intermediate (ac) with a halogen compound (b) being capable of forming the electron donor by replacement of its halogen by said alkoxy moiety.

44 Claims, 9 Drawing Sheets

Figure 1   Example of the first main embodiment

Figure 2    Example of the second main embodiment

Figure 3    Example of the third main embodiment

Correlation between the activity (in kg PP/g cat) and the number of toluene washes used in the catalyst synthesis Correlation between the activity (in kg PP/g Ti) and the number of toluene washes used in the catalyst synthesis Details of IR spectra in the C=O---metal complex region of $TiCl_4 \cdot DUP$ (A), $(MgCl_2)_{1.5} \cdot DOP$ (B), $MgCl_2 \cdot TiCl_4 \cdot D_1$ (C) prepared from $MgCl_2 \cdot 3ROH$, and of $(MgCl_2)_7 \cdot TiCl_4 \cdot DOP$ (D = example 6) prepared from $MgCl_2 \cdot DOP$ in 10 mol $TiCl_4$ Details of IR spectra in the C-O---metal complex region of $TiCl_4 \cdot DUP$ (A), $(MgCl_2)_{1.5} \cdot DOP$ (B), $MgCl_2 \cdot TiCl_4 \cdot D_1$ (C) prepared from $MgCl_2 \cdot 3ROH$, and of $(MgCl_2)_7 \cdot TiCl_4 \cdot DOP$ (D = example 6) prepared from $MgCl_2 \cdot DOP$ and $10\ TiCl_4$ X-ray patterns of Mg(OR)$_2$ (A), MgCl$_2$·TiCl$_4$·DOP (B) produced from MgCl$_2$·3EtOH, and (MgCl$_2$)$_{1.7}$·TiCl$_4$·DOP (C) produced from MgCl$_2$·DOP and 10 TiCl$_4$ IR spectra of examples 9(A) and 10a (B)

X-ray pattern of the catalyst of example 8a

X-ray patterns of examples 9(A) and 10a (B)

X-ray patterns of example 10b, i.e. the toluene washed example 10a

The activities of the catalysts coming from experiments 8b–10b,
1) example 8b, 2) example 9, 3) example 10a and 4) example 10b.
◆ as kg PP/g cat units and ■ as kg PP/g Ti units

CATALYST COMPONENT COMPRISING MAGNESIUM, TITANIUM, A HALOGEN AND AN ELECTION DONOR, ITS PREPARATION AND USE

The invention relates to a process for the preparation of an olefin polymerization catalyst component containing magnesium, titanium, halogen and an electron donor. The invention also relates to such a catalyst component and its use for the polymerization of α-olefins such as propene.

BACKGROUND OF THE INVENTION

Generally, so called Ziegler-Natta catalyst components of the above kind have been prepared by reacting a magnesium halide-alcohol complex with a titanium tetra-halide and an electron donor which usually is a phthalic acid diester. The preparation involves the use of large amounts of reagents and washing liquids, which are difficult to handle. Additionally, byproducts are formed, which cannot easily be regenerated or destroyed, but form an environmental problem.

For example, the preparation of a conventional polypropene catalyst component involves the reaction of a magnesium dichloride-alcohol complex with titanium tetrachloride to give reactive β-magnesium dichloride as intermediate and hydrogen chloride and titanium alkoxy trichloride as byproducts. Then, the reactive β-magnesium dichloride intermediate is activated with further titanium tetrachloride to give said catalyst component (the treatment with a titanium halide such as titanium tetrachloride is henceforth called titanation).

The titanium alkoxy trichloride byproduct formed in the titanation is a catalyst poison and must be carefully removed by extensive washing using large amounts of titanium tetrachloride. Further, the titanium alkoxy trichloride must be carefully separated from the titanium tetrachloride washing liquid, if the latter is to be reused e.g. for activating the reactive β-magnesium dichloride. Finally, the titanium alkoxy trichloride is a problem waste, which is difficult to dispose of.

Thus, in a typical propene polymerization catalyst component preparation involving two titanations and three heptane washes, one mol of produced catalyst component (mol Mg) requires about 40 mol of titanium tetrachloride e.g. as washing liquid to be circulated (see Table 15 below), and produces as problem waste about three mol of titanium alkoxy trichloride as well as about three mol of hydrogen chloride.

Sumitomo, EP 0 748 820 A1 (hereinafter referred to as "Sumitomo"), has prepared dialkoxy magnesium, reacted it with titanium tetrachloride to form an intermediate and then reacted the intermediate with phthalic acid dichloride to form a catalytically active propene polymerization catalyst component. The activity was raised by repeated titanations, as well as repeated washes with toluene and hexane. See page 10, lines 14 to 37, of said publication.

Said process of Sumitomo has avoided the reaction between the magnesium dichloride-alcohol complex and titanium tetrachloride, and thereby eliminated the formation of catalytically poisonous titanium alkoxy trichloride byproduct. However, as much as four titanations and hydrocarbon treatments are still needed to give satisfactory catalytic activity.

DESCRIPTION OF THE INVENTION

The purpose of the present invention is to provide a process which results in a catalyst component having satisfactory activity without producing harmful byproducts such as said titanium alkoxy trichloride or requiring the use of a large amounts of titanation reagent and/or washing liquid.

The problem described above has now been solved with a novel process for the preparation of a catalyst component of the above type, which is mainly characterized by the steps of:

(i) reacting a titaniumless magnesium compound (a) containing an alkoxy moiety, which titaniumless magnesium compound is selected from the group consisting of a compound or conplex containing halogen and alkoxide linked to magnesium, a complex containing a magnesium dihalide and an alcohol, and a non-complex magnesium dialkoxide, with a halogen compound (b) being capable of forming the electron donor by replacement of its halogen by said alkoxy moiety, to give an intermediate (ab); and (ii) reacting said intermediate (ab) with a titanium halide (c), or (i)' reacting a titaniumless magnesium compound (a) containing an alkoxy moiety, which titaniumless magnesium compound is selected from the group consisting of a compound or complex containing halogen and alkoxide linked to magnesium, and a complex containing a magnesium dihalide and an alcohol, with a titanium halide (c), to give an intermediate (ac), and (ii)' reacting said intermediate (ac) with a halogen compound (b) being capable of forming the electron donor by replacement of its halogen by said alkoxy moiety.

It was found by the applicant, that the activity of a stoichiometric catalyst component, comprising a magnesium dihalide, a titanium tetrahalide and an electron donor, is the higher, the more magnesium dihalide it contains. Thus it is believed, that the purpose of the repeated toluene washes of e.g. Sumitomo has partly been to remove titanium tetrachloride and electron donor from the catalyst component precursor in order to raise the magnesium dichloride content and thus the catalytic activity, of the final catalyst component. The present invention solves the problem in another way. In the claimed process, magnesium dihalide is included or synthesized as part of the reacting material before any titanation takes place, and thus, the need for repeated cycles of titanation and washing is significantly reduced.

Preferably one, most preferably all of steps (i), (ii), (i)' and (ii)' are performed in solution. Then, the reaction product of step (ii) or (ii)' is preferably recovered by precipitation.

According to one embodiment of the present invention, said compounds (a), (b) and (c) are in the claimed process contacted in essentially stoichiometric amounts. According to another embodiment, a stoichiometric excess, preferably a 5–20 fold excess, of said titanium halide (c) with respect to said magnesium compound (a), gives even better results.

Said halogen compound (b) used in the claimed process is an electron donor precursor, i.e. itself capable of forming the electron donor of the catalyst component by replacement of its halogen by an alkoxy group. By electron donor is in this connection meant an electron donor which forms a part of the titanous catalyst component produced by the claimed process and is in the art also called an internal electron donor. Such halogen compounds (b) are, e.g., $C_1$–$C_{20}$ alkyl halides, $C_7$–$C_{27}$ aralkyl halides and $C_2$–$C_{22}$ acyl halides, which react with alkoxy compounds to replace their halogen with the alkoxy group of the alkoxy compound and form e.g. the corresponding ethers and esters acting as internal electron donors.

Preferably, said halogen compound (b) is an organic acid halide having the formula R"(COX')$_n$, wherein R" is an n-valent organic group having 1–20 carbon atoms, preferably an n-valent benzene ring, X' is a halogen, preferably chlorine; and n is the valence of R" and is an integer 1 to 6, preferably 1, 2, 3 or 4, more preferably 2. Most preferably, said halogen compound is phthalic acid dichloride Ph(COCl)$_2$, wherein Ph is o-phenylene. Correspondingly, the electron donor formed therefrom is preferably an organic acid ester having the formula R"(COOR)$_n$, wherein R is an n-valent C$_1$–C$_{20}$ aliphatic group or an n-valent C$_7$–C$_{27}$ araliphatic group and R" and n are the same as above, and more preferably a phthalic acid diester Ph(COOR)$_2$, wherein R is a C$_1$–C$_{20}$ alkyl or a C$_7$–C$_{27}$ aralkyl, more preferably a C$_1$–C$_{16}$ alkyl. Most preferably said electron donor is dioctyl phthalate.

The titanium halide (c) used in the claimed process is preferably a titanium halide of the formula (OR')$_k$TiX$_{4-k}$, wherein R' is an alkyl group having 1 to 10 carbon atoms or an aralkyl group having 7 to 16 carbon atoms, X is a halogen and k is 0 to 3. More preferably, said titanium halide (c) is a titanium tetrahalide TiX$_4$, wherein X is the same as above, most preferably titanium tetrachloride TiCl$_4$.

It is preferable, if said titaniumless magnesium compound (a) is not a part of a solid magnesium halide, e.g. in the form of complex molecules on the surface of a solid magnesium halide carrier, but form a separate compound with an essentially stoichiometric composition. Often, said titaniumless magnesium compound is a complex. A complex is, according to Römpps Chernie-Lexicon, 7. Edition, Franckh'sche Verlagshandlung, W. Keller & Co., Stuttgart, 1973, page 1831, "a derived name of compounds of higher order, which originate from the combination of molecules,—unlike compounds of first order, in the creation of which atoms participate".

According to one embodiment of the invention, the titaniumless magnesium compound (a) used in the claimed process is a titaniumless complex of the formula [MgX$_2$]$_x$. [K(OR)$_m$]$_y$, wherein X is a halogen, K is hydrogen, a metal of group 1, 2 or 13 of the Periodic Table, R is an alkyl having 1 to 20 carbon atoms, an aralkyl having 7 to 27 carbon atoms or an acyl having 2 to 22 carbon atoms, x is 0 to 20, m is the valence of K and is an integer from 1 to 6, and y is 1 to 20.

The magnesium dihalide MgX$_2$ of said titaniumless complex (a) can be selected from magnesium chloride, magnesium bromide and magnesium iodide. Preferably, it is magnesium dichloride.

The alkoxy compound K(OR)$_m$ is in its most general form defined as a component of said titaniumless complex (a), which complex (a) is reacted further with said halogen compound (b) and said titanium halide (c) or said titanium halide (c) and said halogen compound (b). The alkoxy compound is, however, more closely defined in the following description of three main embodiments of the claimed process.

The gist of the invention is to choose the reactants and their order of reaction so that the magnesium dihalide is present when the titanium halide (c) is reacted.

BRIEF DESCRIPTION OF DRAWINGS

The invention is further illustrated in the accompanying drawings wherein:

FIG. 9 shows the IR spectra of Examples 9 and 10a.

FIG. 10 shows X-ray pattern of the catalyst of example 8a.

FIG. 11 shows the X-ray patterns of Examples 9 and 10a.

FIRST MAIN EMBODIMENT

Figure 1:
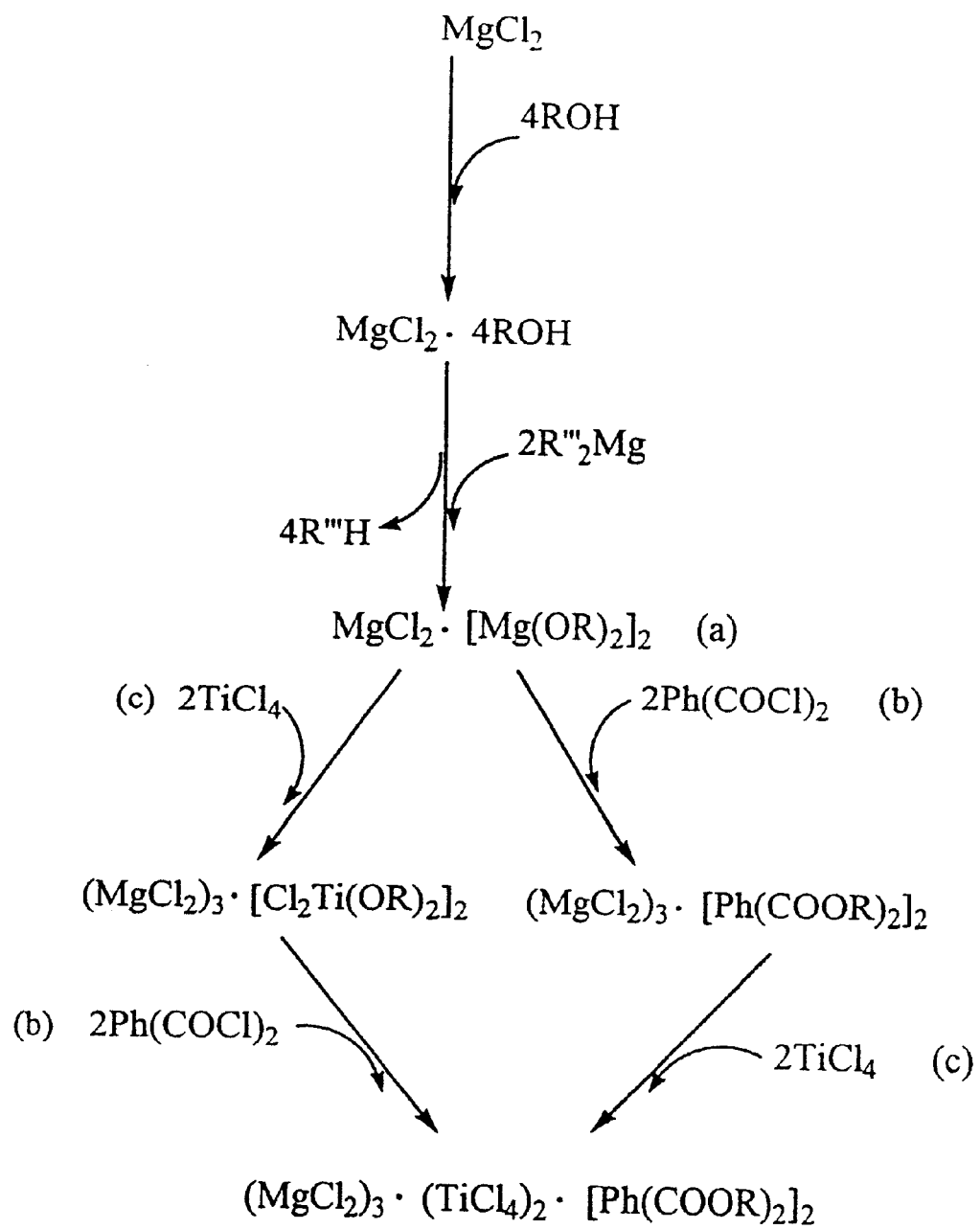
FIG. 1 shows an example of the first main embodiment.

According to a first main embodiment of the invention, said titaniumless magnesium compound (a) is a compound or complex containing halogen and alkoxide linked to magnesium. It may be a compound such as a magnesium haloalkoxide, typically MgXOR.nR'OH, wherein X is a halogen, preferably chlorine, R and R' are a C$_1$–C$_{12}$ hydrocarbyl and n is 0–6. Typically, it is a complex product containing magnesium, halogen and alkoxy, essentially characterized by having the following formula (1):

$$Mg_pX_q(OR)_{2p-q} \quad (1)$$

wherein X is a halogen, preferably a chlorine, R is an alkyl group having from 1 to 20 carbon atoms, p is from 2 to 20 and q is <p, preferably <0.66 p. If there are several halogens X and alkoxy groups OR in the complex product, they can be different or equal.

The complex containing magnesium, halogen and alkoxy used in the invention can, depending on the quality and quantity of elements and groups, preferably be soluble in non-polar organic solvents. The soluble complexes are thus preferably used as starting material for catalytically active stoichiometrical procatalyst complexes. Further, the complex containing magnesium, halogen and alkoxy is always less reductive than magnesium alkyls MgR$_2$ and RMgX and is therefore more suitable for activation of the transition metal compound.

The chemical structure of the titaniumless magnesium compound (a) according to the first main embodiment is based on the bivalence and bridge-forming ability of magnesium. It is believed, without limiting the scope of the invention, that the chemical structure for complexes having p≧3 is (a):

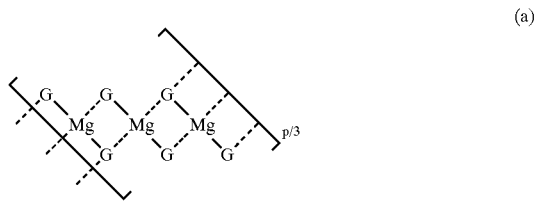

wherein each G is the same or different and is selected from said X and said OR to form q units of X and 2p-q units of OR, and p is from 3 to 20. If p/3 is greater than 1 there is in formula (a) a . . . -bridge from the furthest Mg—G to the nearest Mg—G of the next unit.

The chemical structure can also be (b):

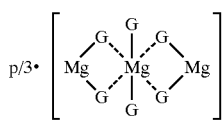

wherein each G is the same or different and is selected from said X and said OR to form q units of X and 2p−q units of OR, and p is from 3 to 20, or (c):

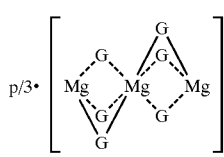

wherein each G is the same or different and is selected from said X and said OR to form q units of X and 2p−q units of OR, and p is from 3 to 20.

When the titaniumless magnesium compound (a) has the composition and structure according to the first main embodiment, the claimed process takes place as follows:
(i) said complex containing halogen and alkoxide linked to magnesium as said titaniumless magnesium compound (a) is reacted with said halogen compound (b) to give an intermediate (ab) and then
(ii) said intermediate (ab) is reacted with said titanium halide (c), i.e. [(a)+(b)]+(c), or:
(i)' said complex containing halogen and alkoxide linked to magnesium as said titaniumless magnesium compound (a) is reacted with said titanium halide (c) to give an intermediate (ac) and then
(ii)' said intermediate (ac) is reacted with said halogen compound (b), i.e. [(a)+(c)]+(b).

In both contact sequences a titaniumless compound containing halogen linked to magnesium is, contrary to Sumitomo, reacted with a titanium halide. When repeating Sumitomo, it gave poorer results than the invention.

In said first main embodiment, said complex is preferably a complex of a magnesium dihalide and a magnesium dialkoxide as said magnesium compound (a). More preferably, it is a magnesium dichloride-magnesium alkoxide complex having the formula $MgCl_2 \cdot [Mg(OR)_2]_t$, wherein R is a $C_1$–$C_{20}$ alkyl or a $C_7$–$C_{27}$ aralkyl, preferably a $C_6$–$C_{16}$ alkyl, and t is 1–6, preferably about 2. It is e.g. prepared by reacting magnesium dichloride $MgCl_2$ with an alcohol ROH into an intermediate which is a magnesium dichloride-alcohol complex $MgCl_2 \cdot (ROH)_{2t}$ and reacting the magnesium dichloride-alcohol complex with t mol of a magnesium dialkyl $MgR'''_2$, wherein R''' is a hydrocarbyl group having 1 to 20 carbon atoms.

Most preferably, the complex of said magnesium dihalide and a magnesium di-alkoxide as said alkoxy compound is a magnesium dichloride-dimagnesium di-alkoxide complex having the formula $MgCl_2 \cdot [Mg(OR)_2]_2$, wherein R is a $C_1$–$C_{20}$ alkyl or a $C_7$–$C_{27}$ aralkyl, preferably a $C_6$–$C_{16}$ alkyl. The complex may e.g. be prepared by reacting magnesium dichloride with an alcohol ROH and the obtained intermediate with a dialkyl magnesium R'''$_2$Mg essentially as follows:

$$MgCl_2 + 4ROH \rightarrow MgCl_2 \cdot 4ROH$$

$$MgCl_2 \cdot 4ROH + 2MgR'''_2 \rightarrow MgCl_2[Mg(OR)_2]_2 + 4R'''H$$

In the reaction between the magnesium dihalide, the alcohol and the dialkyl-magnesium, the molar ratio $MgCl_2$:ROH is preferably 1:1 to 1:8, most preferably 1:2 to 1:5. The molar ratio $MgCl_2 \cdot 4ROH$:$MgR'''_2$ is preferably 1:1 to 1:4, most preferably about 1:2. The temperature is preferably 100° C. to 200° C. and the reaction time preferably about 2 h to about 8 h. A hydrocarbon solvent such as toluene may be present in the reaction.

Most probably the complex has the structure of an equilibrium between structures ($a_1$), ($a_2$), (b) and (c), as illustrated (non-limiting) by the following trimer equilibrium of the $MgCl_2 \cdot [Mg(OR)_2]_2$ complex:

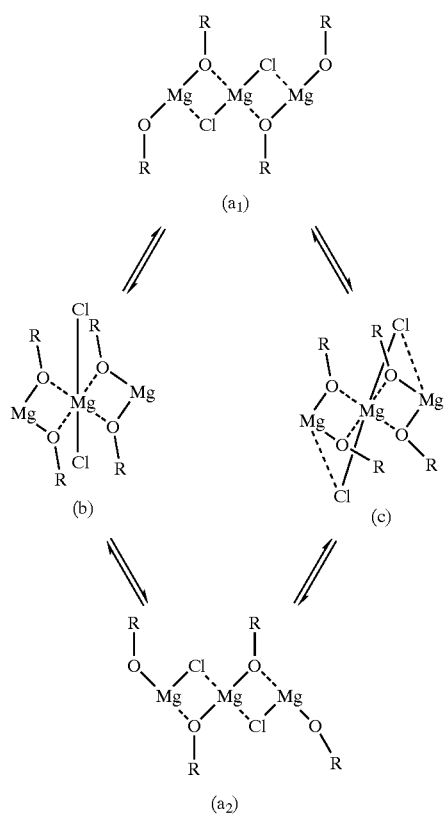

In the above formulas ($a_1$), ($a_2$), (b) and (c), Cl can be replaced by any halogen such as fluorine, chlorine, bromine and iodine, but the purposes of the invention are best fulfilled with chlorine.

The alkyl R of the alkoxy group can be any alkyl suitable for the purpose of the invention. Similar structure and solubility parameter to optional solvents give soluble complexes for stoichiometric preparation of active procatalyst complexes. Different structure and solubility parameters give insoluble complexes for use as activating support. When a solvent having 5–10 carbon atoms, such as toluene, is used, R is preferably an alkyl group having from 1 to 16 carbon atoms, more preferably from 4 to 12 carbon atoms, most preferably from 6 to 10 carbon atoms.

According to the most preferable variant of said first main embodiment:
(i)' said magnesium dichloride-dimagnesium dialkoxide complex $MgCl_2 \cdot [Mg(OR)_2]_2$ (a) wherein R is a $C_1$–$C_{20}$ alkyl or a $C_7$–$C_{27}$ aralkyl, preferably a $C_6$–$C_{16}$ alkyl is reacted with said titanium halide (c), which is said titanium tetrachloride $TiCl_4$, to give an intermediate (ac) and then (ii)' said intermediate (ac) is reacted with said halogen compound (b), which is said phthalic acid dichloride $Ph(COCl)_2$, wherein Ph is o-phenylene.

The reactions of this variant can, without limiting the scope of protection, e.g. be described by means of the following equations:

Step (1'):

$$MgCl_2 \cdot [Mg(OR)_2]_2 + 4/q TiCl_4 \rightarrow (MgCl_2)_3 \cdot [Cl_{4-q}Ti(OR)_4]_{4/q}$$

Step (2'):

$$(MgCl_2)_3[Cl_{4-q}Ti(OR)_q]_{4/q} + 2Ph(COCl)_2 \rightarrow (MgCl_2)_3 \cdot (TiCl_4)_{4/q} \cdot [Ph(COOR)_2]_2$$

Usually, q is 1 or 2. It can e.g. be seen, that the harmful $Cl_3TiOR$ (when q=1) after it is formed remains complexed and is finally converted to catalytically active $TiCl_4$. No purification or waste problems relating to the formation $Cl_3TiOR$ arise.

In step (ii) of said first main embodiment, said intermediate (ab) and/or said complex of said magnesium dihalide and a magnesium alkoxide as said magnesium compound (a), respectively, are preferably added to the titanium halide (c), and not vice versa. Even more preferably, they are added drop by drop, to said titanium halide (c). The titanium halide (c) is preferably in liquid form and most preferably hot, such as at 70–140° C.

In said first main embodiment, the molar ratio between the reactants (a), (b) and (c) is preferably approximatively stoichiometric with the exception of the titanium halide (c) in step (ii) which preferably is used in a 5 to 20 fold excess with respect to the magnesium halide. Elevated temperatures are preferably used, whereby said halogen compound (b) preferably is reacted at 50° C. to 75° C. and said titanium halide (c) in step (ii) preferably is reacted at 70° C. to 110° C.

Although the first main embodiment reduces the need for repeated titanations and washes, a still more active and pure product is obtained if the titanation and hydrocarbon wash are repeated 1 to 3 times.

An example of the first main embodiment is presented in an enclosed scheme, see FIG. 1.

SECOND MAIN EMBODIMENT

According to a second main embodiment of the invention, said titaniumless magnesium compound (a) is a complex of said magnesium dihalide and an alcohol carrying said alkoxy moiety, or, alternatively, a non-complex magnesium di-alkoxide.

The claimed process then takes place as follows:
(i) said titaniumless magnesium compound (a) which is selected from said complex of said magnesium dihalide and said alcohol, and said non-complex magnesium dialkoxide, is reacted with said halogen compound (b) to give an intermediate (ab) which is a complex of a magnesium dihalide and said electron donor and
(ii) said intermediate (ab) which is a complex of said magnesium dihalide and said electron donor is reacted with said titanium halide (c).

In a first variant of said second main embodiment, a non-complex magnesium di-alkoxide is used as the starting material (a) of step (i). It is preferably a magnesium dialkoxide $Mg(OR)_2$, wherein R is a $C_1$–$C_{20}$ alkyl or a $C_7$–$C_{27}$ aralkyl, preferably a $C_6$–$C_{16}$ alkyl. It can be prepared by any suitable process such as the process described by Sumitomo, see column 9, line 56, to column 10, line 13. In the present invention, however, it is preferably prepared by reacting a magnesium dialkyl and an alcohol ROH. The reaction can e.g. be described by means of the following equation:

$$MgR'''_2 + 2ROH \rightarrow Mg(OR)_2 + 2R'''H\uparrow$$

wherein R and R''' are as defined above.

In the first variant of said second main embodiment, the most preferable process comprises the steps wherein:
(i) said titaniumless magnesium compound (a), which is said magnesium di-alkoxide $Mg(OR)_2$, wherein R is a $C_1$–$C_{20}$ alkyl or a $C_7$–$C_{27}$ aralkyl, preferably a $C_6$–$C_{16}$ alkyl, is reacted with said halogen compound (b), which is said phthalic acid dichloride $Ph(COCl)_2$, wherein Ph is o-phenylene; to give an intermediate (ab) which is a complex of said magnesium dichloride and said phthalic acid diester $Ph(COOR)_2$, and
(ii) said intermediate (ab), which is said complex of said magnesium dichloride and said phthalic acid diester $Ph(COOR)_2$, is reacted with said titanium halide (c), which is said titanium tetrachloride $TiCl_4$.

The reactions can, without limiting the scope of protection, e.g. be described by means of the following equations:

Step (i):

$$Mg(OR)_2 + Ph(COCl)_2 \rightarrow MgCl_2 \cdot Ph(COOR)_2,$$

and
Step (ii):

$$MgCl_2 \cdot Ph(COOR)_2 + m'TiCl_4 \rightarrow MgCl_2 \cdot (TiCl_4)_{m'} \cdot Ph(COOR)_2$$

wherein m' is about 1 to about 2.

In a second variant of said second main embodiment, a complex of said magnesium dihalide and an alcohol is used as said titaniumless magnesium compound (a) of step (i). It is preferably a magnesium dichloride alcohol complex $MgCl_2 \cdot (ROH)_m$, wherein R is a $C_1$–$C_{20}$ alkyl or a $C_7$–$C_{27}$ aralkyl preferably a $C_6$–$C_{16}$ alkyl, and m is 1–6. The complex is preferably prepared by reacting magnesium dichloride and an alcohol, e.g. as illustrated by the following equation:

$$MgCl_2 + mROH \rightarrow MgCl_2 \cdot (ROH)_m$$

In the second variant of said second main embodiment, the most preferable process then comprises the steps wherein:
(i) said titaniumless magnesium compound (a), which is said magnesium di-chloride-alcohol complex $MgCl_2 \cdot (ROH)_m$, wherein R is a $C_1$–$C_{20}$ alkyl or a $C_7$–$C_{27}$ aralkyl, preferably a $C_6$–$C_{16}$ alkyl and m is 1–6, is reacted with said halogen compound (b), which is said phthalic acid dichloride $Ph(COCl)_2$, wherein Ph is o-phenylene, to give an intermediate (ab), which is a complex of said magnesium dichloride and said phthalic acid diester $Ph(COOR)_2$, wherein R is the same as above, and
(ii) said intermediate (ab) which is said complex of said magnesium dichloride and said phthalic acid diester $Ph(COOR)_2$, is reacted with said titanium halide (c), which is said titanium tetrachloride $TiCl_4$.

The reactions can, without limiting the scope of protection, be described by means of the following equations:

Step (i):

$MgCl_2 \cdot (ROH)_m + m/2 \cdot Ph(COCl)_2 \rightarrow MgCl_2 \cdot [Ph(COOR)_2]_{m/2} + mHCl \uparrow$ Step (ii):

$MgCl_2 \cdot [Ph(COOR)_2]_{m/2} + m'TiCl_4 \rightarrow MgCl_2 \cdot (TiCl_4)_{m'} \cdot [Ph(COOR)_2]_{m2}$ wherein m is 1–6 and mn is from 0.5 to m.

In step (ii) of said second main embodiment, said complex of said magnesium dihalide and said electron donor is preferably added to the titanium halide (c), and not vice versa. Even more preferably, it is added drop by drop, to said titanium halide (c). The titanium halide (c) is preferably in liquid form and most preferably hot, such as at 70–140° C.

In said second main embodiment, the molar ratio between the reactants (a), (b) and (c) is approximatively stoichiometric, preferably with the exception of the titanium halide (c) which more preferably is used in a 5 to 20 fold excess with respect to the magnesium halide. Elevated temperatures are preferably used, whereby said halogen compound (1) preferably is reacted at 50° C. to 75° C. and said titanium halide (c) preferably is reacted at 70° C. to 110° C.

Although said second embodiment reduces the need for repeated titanations and washes, a still more active and pure product is obtained if the titanation and hydrocarbon wash are repeated 1 to 3 times.

Figure 2:
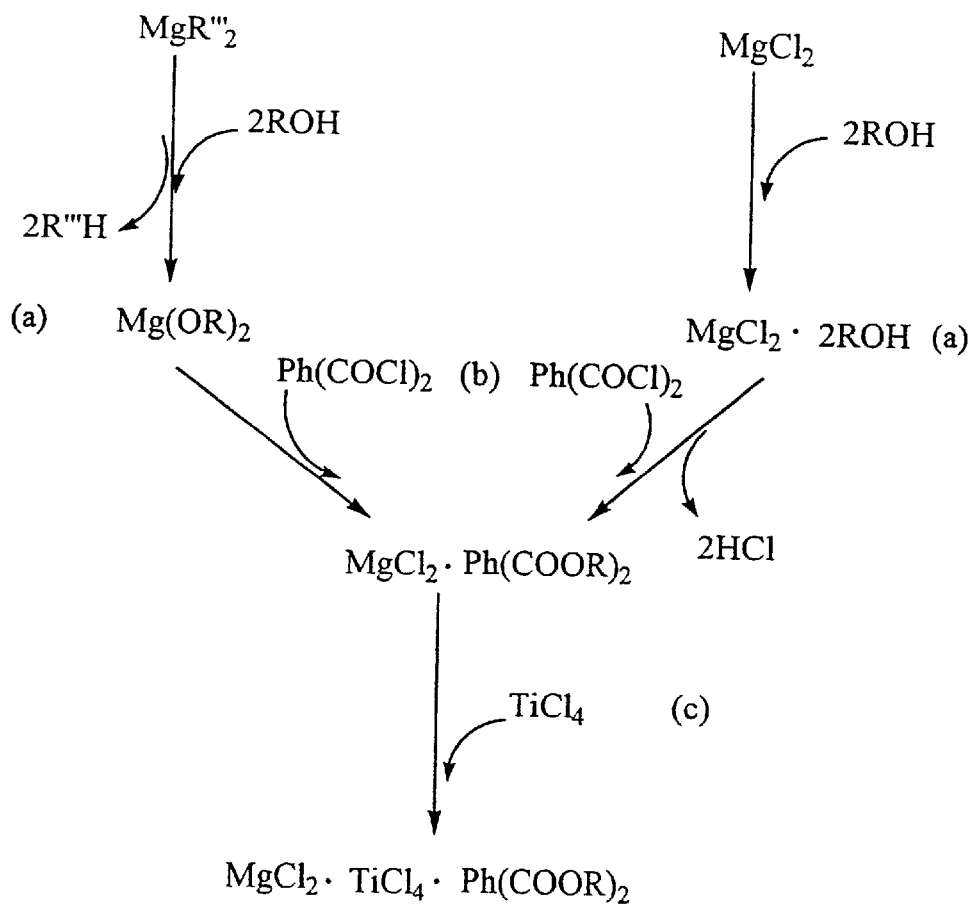
FIG. 2 shows an example of the second main embodiment.

An example of the second main embodiment is presented in an enclosed scheme, see FIG. 2.

THIRD MAIN EMBODIMENT

According to a third main embodiment of the invention, said titaniumless magnesium compound (a) is a complex of said magnesium dihalide and an alcohol carrying said alkoxy group.

In that case:

(i)' said titaniumless magnesium compound (a) which is said complex of said magnesium dihalide and an alcohol, is reacted with said titanium halide (c), to give an intermediate (ac), and (ii)' said intermediate (ac) is reacted with said halogen compound (b).

In the third main embodiment, the complex of said magnesium dihalide and an alcohol is preferably a magnesium dichloride-alcohol complex $MgCl_2 \cdot (ROH)_m$, wherein R is a $C_1$–$C_{20}$ alkyl or a $C_7$–$C_{27}$ aralkyl and m is 1–6. It can be prepared as described above.

According to the most preferable variant of said third embodiment, the process comprises the following steps:

(i) titaniumless magnesium compound (a), which is said magnesium dichloride-alcohol complex $MgCl_2 \cdot (ROH)_m$, wherein R is a $C_1$–$C_{20}$ alkyl or a $C_7$–$C_{27}$ aralkyl and m is 1–6, is reacted with said titanium dihalide (c), which is said titanium tetrachloride $TiCl_4$, to give an intermediate (ac) and (ii)' said intermediate (ac) is reacted with said halogen compound (b), which is said phthalic acid dichloride $Ph(COCl)_2$ wherein Ph is o-phenylene.

This reaction can, without limiting the scope of protection, e.g. be described by means of the following equation:

Step (i)':

$MgCl_2 \cdot (ROH)_m + m/q \cdot TiCl_4 \rightarrow MgCl_2 \cdot [Cl_{4-q}Ti(OR)_q]_{m/q}$ Step (ii)':

$MgCl_2 \cdot [Cl_{4-q}Ti(OR)_q]_{m/q} + m/2 \cdot Ph(COOH)_2 \rightarrow MgCl_2 \cdot (TiCl_4)_{m/q} \cdot [Ph(COOR)_2]_{m/2}$ wherein m is from about 1 to about 6, preferably about 2, q is 1–4, preferably about 2, and R is as said above.

In step (i)' of said third main embodiment, said titanium halide (c) is preferably added to said complex of said magnesium dihalide and an alcohol as said titaniumless magnesium compound (a), and not vice versa. Even more preferably, it is added drop by drop, to said titaniumless magnesium compound (a). The titanium halide (c) is preferably in liquid form.

In said third main embodiment, the molar ratio between the reactants (a), (b) and (c) is preferably approximatively stoichiometric.

Although said third embodiment reduces the need for repeated titanations and washes, a still more active and pure product is preferably obtained if the final titanation and hydrocarbon (e.g. toluene) wash are repeated 1 to 3 times.

Figure 3:
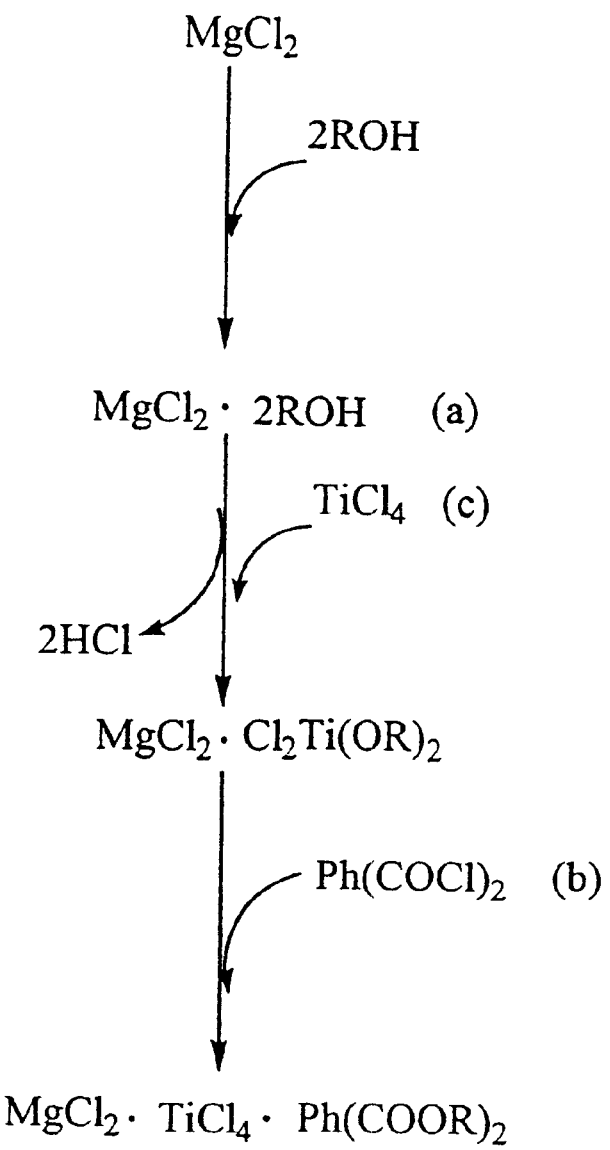
FIG. 3 shows an example of the third main embodiment.

An example of the third main embodiment is presented in an enclosed scheme, see FIG. 3.

As was stated above, common to the first and second main embodiments is, that in step (ii) said intermediate (ab) is preferably added, more preferably drop by drop, to said titanium halide (c), which is in liquid form and preferably hot, more preferably at 75–150° C. Further, all embodiments may further comprise a step wherein:

(iii) the obtained product of step (ii) or (ii)' is further treated with said titanium halide (c) and/or washed, preferably repeatedly washed with an aromatic hydrocarbon, such as toluene, or an organic liquid having the same solubility parameter as said aromatic hydrocarbon.

The washing can, without limiting the scope of protection, be illustrated by the following equation:

$x[MgCl_2 \cdot TiCl_4 \cdot Ph(COOR)_2] + $ toluene $ \rightarrow (MgCl_2)_x \cdot TiCl_4 \cdot Ph(COOR)_2 + (x-1)TiCl_4 \cdot Ph(COOR)_2 + $ toluene  (product)

x is a number larger than 1.

It is seen that the $MgCl_2$ is concentrated in the catalyst component, which leads to higher activity.

Product and Use

In addition to the above described process, the invention also relates to a catalyst component comprising magnesium, titanium, a halogen and an electron donor. The catalyst component is characterized in that it has been prepared by the process described in any of claims 1 to 15 or in the preceding text. Preferably, the claimed catalyst component is an isolated complex of a magnesium dihalide, preferably magnesium dichloride, an electron donor obtained by replacing the halogen of a halogen compound by an alkoxy group, preferably a phthalic acid diester, and a titanium halide, preferably titanium tetrachloride. Preferably, said complex is prepared by contacting stoichiometric amounts of said components (a), (b) and (c). Preferably, said complex has an X-ray pattern comprising a peak between 5° and 10° 2θ (Siemens D500 instrument, CuKα radiation wavelength 1.541 Å, effect 40 kV and 35 mA). Most preferably, said complex has an X-ray pattern comprising a crystal height indicating peak between 16° and 18° 2θ.

The invention also relates to the use of said catalyst component for the polymerization of α-olefins, preferably propene. In such a polymerization, said catalyst component is preferably used together with another catalyst component comprising an organometal compound of a metal belonging to Group 1, 2 or 13 (IUPAC 1990) of the Periodic Table, preferably an alkyl aluminium compound, is used. The organometal compound is in the art called a cocatalyst. Further, another electron donor may be used together with said catalyst component and the co-catalyst. Such a donor is in the art called an external electron donor.

EXAMPLES 1 TO 4

First Main Embodiment
Preparation of the Catalyst Component Complex 1.69 g (17.70 mmol) of anhydrous $MgCl_2$ was introduced in inert conditions into a 100 ml septum bottle. 11.12 ml (9.27 g, 70.80 mmol) of 2-ethyl-hexanol (EHA) was introduced on to the $MgCl_2$ and after this the temperature was increased to 125–128° C. to allow the reaction components to react with each other. After this, 8.81 ml (7.67 g, 83.19 mmol) of toluene was added after the reaction solution had cooled down to 110° C. After the addition of the toluene the reaction solution was cooled down to 21° C. Then 40 ml (29.16 g, 35.4 mmol) of a 20 w-% heptane solution of butyl-octyl-magnesium (BOMAG) was added. After this 5.10 ml (7.19 g, 35.4 mmol) of phthaloyl dichlorid (PDC) was added to produce a $MgCl_2$ donor complex solution.

The $MgCl_2$ donor complex was now, drop by drop, added into 38.91 ml (67.16 g, 354 mmol) of $TiCl_4$ and allowed to react with this reagent at a temperature of 95° C. The reactants were allowed to react with each other for 30 min.

After the $TiCl_4$ treatment, the complex was allowed to settle and the liquid was siphoned off. After this, 100 ml (86.6 g, 0.94 mol) of toluene was added on to the complex and the complex was washed in this solution at 90° C. for 20 min. Depending on which of the synthesis was under work, this washing step was done once (example 1), twice (example 2), three times (example 3) or four times (example 4). Finally, the catalyst complex was washed twice with 65 ml (44.44 g, 0.44 mol) portions of heptane for 20 min at 80° C. and thereafter, the complex was washed at room temperature with a 55 ml (34.44 g, 0.48 mol) portion of pentane for 20 min to improve the drying conditions. The catalysts were dried under a stream of nitrogen for one hour.

Chemical Characterization of the Complexes

The catalyst complexes were characterized with respect to their chemical composition by measuring their Ti and Cl content. The Ti analysis was started by dissolving the samples in a mixture of nitric and hydrofluoric acid. The metal was measured flame atomic absorption with a nitrous acetylene flame. Chloride was determined after dissolution in dilute sulphuric acid by potentiometric titration with a standard silver nitrate solution.

Determination of Donors and Phthalic Anhydride

The determination of the phthalic esters and the phthalic anhydride were done by first dissolving the sample in acetone. The dissolving was improved by keeping the acetone slurry in an ultrasound bath for 5 min. After this the samples were filtered and run by solution chromatography. As eluent a solution consisting of water and acetonitril in the proportion of 4/96 was used. Eluent flow rate was 1.5 ml/min. A photo diode array was used as detector. Each component was identified by comparing the respective retention time and UV spectra with standard components.

GC Studies to Measure Alcohol Content

To check the conversion rate of the ethanol (EtOH), 2-ethyl-hexanol (EHA), or other alcohol added in the synthesis, the alcohol content of the catalysts were measured by gas chromatography (GC). This was done by first dissolving a 100 mg sample of the catalyst in 1 ml of n-pentanol. Depending on the alcohol to be measured, an internal alcohol standard was chosen. If ethanol was to be measured the n-pentanol solution contained n-propenol as internal standard. To improve the solubility of the catalyst in the solution, the sample was kept in an ultra-sound bath. To remove the inorganics from the organic solution it was extracted with 1 ml of water and to ensure fall dissolution, another ml of the n-pentanol solution was added. To ensure repeatable equilibrium conditions between the organic layer and the water layer the samples were allowed to stand overnight. The sample for the GC was taken from the alcohol layer. A Hewlett Packard 5890 GC with a 60 m DB-1 column was used for the GC analyses. The column had a diameter of 0.25 mm with a film thickness of 1 $\mu$m. An FID detector was used.

Bulk Polymerization

Propylene was polymerized in stirred tank reactor having a volume of 5 l. About 0.9 ml triethyl aluminium (TEA) as a cocatalyst, ca 0.12 ml of a 100-% solution of cyclohexyl methyl dimethoxy silane as an external donor and 30 ml of n-pentane were mixed and allowed to react for 5 minutes. Half of the mixture was added to the polymerization reactor and the other half was mixed with ca 20 mg of a catalyst complex. After additional 5 minutes the catalyst/TEA/donor/n-heptane mixture was introduced into the reactor. The Al/Ti mole ratio was 250 and the Al/external donor mol ratio was 10 mol/mol. 70 mmol hydrogen and 1400 g of propylene were introduced into the reactor and the temperature was raised within 15–30 minutes to 70° C. The polymerization time was 60 minutes, after which the polymer formed was taken out from the reactor. The polymers were characterized with respect to their Melt Flow Rate ($MFR_2$), bulk density (BD) and fraction of total solubles in xylene (TS).

Results
Preparation of the Complexes

The catalyst complexes achieved in this investigation are listed in Table 1.

TABLE 1

The catalyst complexes prepared.

| Example | Number of toluene washes | Colour of catalyst | Morphology of catalyst |
|---------|--------------------------|--------------------|-----------------------|
| 1 | 1 | Dark wine-red | Freely flowing |
| 2 | 2 | Dark wine-red | Freely flowing |
| 3 | 3 | Dark wine-red | Freely flowing |
| 4 | 4 | Dark wine-red | Freely flowing |

The Chemical Composition of the Catalysts

The chemical composition of the catalysts were measured according to the description in the experimental section. In Table 2 the chemical composition of the catalysts are listed in w-% units, in Table, 3 the composition is listed in mol-% units and in Table 4 the molar proportions between Mg, Ti and DOP are compared.

With three washes a composition of $(MgCl_2)_6TiCl_4DOP$ was achieved. During the washes, there was a slightly higher wash out of $TiCl_4$ compared to DOP in the last catalyst. The amount of free alcohol (EHA) was also very low playing no significant part in the chemical composition (now 0.004–0.006 mol-%), i.e. being about 5% of the mol amount of $TiCl_4$ or DOP. The amount of phthalic anhydride was about 50% of the DOP amount. To sum up the results from the chemical measurements it can be said that the chemical composition of the catalyst complex when using the $MgCl_2$ enriched $Mg(OR')_2$ as a reagent in the catalyst synthesis is $(MgCl_2)_3TiCl_4DOP(PA)_{0.5}$.

TABLE 2

The chemical composition of the catalysts in w-% units

| Example | Mg w-% | Ti w-% | DOP w-% | EHA w-% | PA w-% |
|---|---|---|---|---|---|
| 1 | 7.8 | 4.7 | 33.6 | 0.72 | 6.7 |
| 2 | 8.1 | 4.7 | 32.0 | 0.54 | 7.4 |
| 3 | 10.2 | 3.2 | 28.5 | 0.58 | 6.5 |
| 4 | 12.9 | 1.6 | 21.6 | 0.51 | 6.1 |

TABLE 3

The chemical composition of the catalysts in mol-% units

| Example | Mg mol-% | Ti mol-% | DOP mol-% | EHA mol-% | PA mol-% |
|---|---|---|---|---|---|
| 1 | 0.321 | 0.098 | 0.086 | 0.0055 | 0.045 |
| 2 | 0.333 | 0.098 | 0.082 | 0.0041 | 0.050 |
| 3 | 0.420 | 0.067 | 0.073 | 0.0045 | 0.044 |
| 4 | 0.531 | 0.033 | 0.056 | 0.0039 | 0.041 |

TABLE 4

The molar composition between Mg, Ti and DOP

| Example | Mg | Ti | DOP |
|---|---|---|---|
| 1 | 3.3 | 1 | 0.9 |
| 2 | 3.4 | 1 | 0.8 |
| 3 | 6.3 | 1 | 1.1 |
| 4 | 15.9 | 1 | 1.7 |

Calculated and Found Chlorine Contents

The chlorine content in the catalysts were calculated on the basis of the Mg and Ti content. The calculations were based on the assumption the Mg was present in the catalyst as $MgCl_2$ and Ti as $TiCl_4$. These calculated results were then compared to the measured results. The results are listed in Table 5. The results showed to be in good agreement, which indicates that both Mg and Ti are present in the catalyst complexes in the fully chlorinated form.

TABLE 5

The calculated and the found chlorine content in the catalysts

| Example | Calculated Cl w-% | Found Cl w-% |
|---|---|---|
| 1 | 36.7 | 36.9 |
| 2 | 37.6 | 38.0 |
| 3 | 39.3 | 39.7 |
| 4 | 42.4 | 43.8 |

Wash Out of $TiCl_4 \cdot DOP$

All the chemical measurements support the same conclusion: due to the toluene $TiC_4$ and DOP are washed out from the catalyst in a molar proportion of 1:1. This shows up as a constant decrease of the Ti mol-% and the DOP mol-%, and as a constant increase of the Mg mol-% and the Cl mol-%.

Activity of the Catalysts

All the catalyst complexes were test polymerized according to the descriptions m the experimental section. The results are listed in Table 5. The results showed that all the catalyst complexes had about the same activity, being between 1.0 and 1.5 kg PP/g cat.

TABLE 6

The test polymerization results

| Example | Activity kg PP/g cat | Activity kg PP/g Ti |
|---|---|---|
| 1 | 1.1 | 23 |
| 2 | 1.2 | 26 |
| 3 | 1.5 | 45 |
| 4 | 1.3 | 81 |

MFR of the Polymers

In Table 7 the MFR values achieved from the test polymerization results are listed. The results indicated a systematic increase in MFR with increasing number of toluene washes as MFR increases from 2.0 in the first polymer to 13.7 in the third.

TABLE 7

The MFR values of the polymers

| Example | MFR |
|---|---|
| 1 | 2.0 |
| 2 | 4.9 |
| 3 | 13.7 |
| 4 | 12.4 |

EXAMPLES 5 TO 9

Second Main Embodiment
Preparation of the Catalyst Component Complexes

All chemicals were handled in strict inert conditions and all the reactions took place also in strict inert conditions in nitrogen atmosphere.

8.85 mmol of butyl-octyl-magnesium was introduced into a 150 ml glass reactor. A 20% heptane solution (BOMAG-A) was used giving a feed volume of 10 ml (7.29 g). 17.7 mmol (2.78 ml, 2.32 g) of 2-ethyl-1-hexanol (EHA) was then added at room temperature. The temperature was increased to 60° C. and the reactants were allowed to react with each other at that temperature for 30 min. After this 8.85 mmol (1.28 ml, 1.80 g) of phthaloyl chloride (PDC) was added and the reactants were again allowed to react with each other for 30 min at 60° C. The resulting solution was added dropwise into 88.5 mmol (9.73 ml, 16.79 g) of $TiCl_4$ that had been preheated to 95° C. The reactants were also in this case allowed to react with each other for 30 min at 95° C. After this 60 ml of toluene was added. After the precipitate had settled the mother liquid was siphoned off. Five different examples were carried out according to this description. After this the catalyst complex was washed with 30 ml portions of toluene. In example 5, the complex was washed once with toluene, in example 6 twice, in example 7 three times, in example 8 four times and in example 9 six times with 30 ml portions of toluene. The toluene washes were carried out at 90° C. Last the complex was washed three times with 30 ml portion of pentane. The complexes were finally dried under a stream of nitrogen. The yield of the catalyst was about 2 g which corresponded to about 75% of the theoretical.

Characterization of the Catalyst Components

The catalyst component complexes were analyzed with respect to their Mg, Cl and Ti content. In addition to this, the amount of donor compound, the di-otyl-phthalate (DOP) formed in the synthesis, was measured from the catalysts. To indicate to what degree the formed donor compound (DOP)

was decomposing in the synthesis, the amount of phthalis anhydride (PA) was also measured from the catalysts.

IR and X-ray of the Unwashed Mg:Ti:DOP Complex

A stoichiometric complex of $MgCl_2.TiCl_4.DOP$ was prepared by reacting 6.37 mmol (7.19 ml, 5.24 g) of BOMAG with 12.729 mmol (2.00 ml, 1.67 g) of EHA in a 50 ml glass reactor. After this 6.37 mmol (0.92 ml, 1.29 g) of phthaloyl chloride was introduced and last 6.37 mmol (0.70 ml, 1.21 g) of $TiCh_4$ was added. The solid product was washed with pentane and finally, the sample was dried in a stream of nitrogen. The sample was characterized by IR spectroscopy and by means of its X-ray diffraction pattern.

The IR Studies

IR spectres were taken by means of a Nicolet 510 FTIR equipment with 2 $cm^{-1}$ resolution. The number of scans were 128. All the samples were investigated as capillary films between two KBr tablets. The pure EHA was not handled in inert conditions, while the $MgCl_2$ samples were handled in a glove box in an inert nitrogen environment in order to protect the samples from air and moisture.

X-ray Diffraction Patterns

The WAXS patterns were collected in a reflection mode between 2° and 70° 2Θ with a Siemens D500 instrument. The diffractometer was equipped with a Cu anode and a graphite monochromator in the reflected beam. The CuKα radiation wavelength was 1.541 Å. The effect used was 40 kV and 35 mA. The sample was loaded in a glovebox into a Mylar film covered sample holder.

Bulk Polymerization

The bulk test polymerization was carried out according to the description on page 18.

Results

Preparation of the Complexes

The reaction between the Mg-alkyl and the alcohol resulted in a clear solution with a little bit higher viscosity. The reaction was exothermic as the solution became warm when mixing the reactants, the temperature increase was from room temperature up to 50° C. When the phthaloyl chloride was added a slight yellow colour appeared. Also this reaction was slightly exothermic. The reaction solution become again freely flowing with a low viscosity.

The $TiCl_4$ was introduced into a 150 ml glass reactor and heated to 95° C. The Mg solution was then added to the hot $TiCl_4$ solution dropwise. A beige precipitate started to form right at the beginning of the addition. During addition the solution turned turbid. A partly freely floating precipitate was formed together with more tarlike precipitate that started to foal the reactor walls. To improve the settling conditions toluene was added to the reaction solution. A satisfactory settling of the product was then achieved so that the reaction solution could be siphoned off. Depending on the number of toluene washes; the resulting product become more freely flowing. If only one toluene wash was used the product was still as agglomerates, but already two toluene washes resulted in a freely flowing powder-like product.

In the case of the catalyst components of examples 5, 6 and 7, a joined $MgCl_2$-DOP complex and, a joined addition to the $TiCl_4$ solution was carried out. After the first toluene wash, ⅓ of the solution slurry was separated. The separated part was then washed with the aliphatic hydrocarbon and dried to give the product of example 5. The remaining part of the slurry was washed a second time with toluene and half of this solution slurry was then taken out from the reactor and undertaken the same hydrocarbon treatment as in example 5, resulting in the product of example 6. The remaining part of the catalyst slurry in the reactor was washed twice with toluene and then washed with an aliphatic hydrocarbon in the same way as the first two examples. This sample was the product of example 7. The catalyst morphologies are listed in Table 8.

TABLE 8

The morphology of the catalysts

| Example | Number of toluene washes | Morphology of catalyst |
|---|---|---|
| 5 | 1 | Black agglomerates |
| 6 | 2 | Dark powder |
| 7 | 4 | Dark powder |

The Chemical Composition of the Catalysts

The Mg, Ti, Cl, DOP, EHA and the phthalic anhydride (PA) content of the catalysts were measured. The results are listed in w-% units in Table 9. In Table 10 the chemical composition is given in mol-% units and in Table 11 the Mg and DOP amounts are compared to the Ti amount on a molar basis. Table 12 shows the Cl content of the catalysts.

TABLE 9

The chemical composition of the catalysts in w-% units

| Example | Mg w-% | Ti w-% | DOP w-% | EHA w-% | PA w-% |
|---|---|---|---|---|---|
| 5 | 5.7 | 6.8 | 47.7 | 0.26 | 3.4 |
| 6 | 11.3 | 3.1 | 32.2 | 0.18 | 2.5 |
| 7 | 13.4 | 1.4 | 21.3 | 0.25 | 1.7 |

TABLE 10

The chemical composition of the catalysts in mol-% units

| Example | Mg mol-% | Ti mol-% | DOP mol-% | EHA mol-% | PA mol-% |
|---|---|---|---|---|---|
| 5 | 0.235 | 0.142 | 0.122 | 0.002 | 0.023 |
| 6 | 0.465 | 0.065 | 0.083 | 0.001 | 0.017 |
| 7 | 0.551 | 0.029 | 0.055 | 0.002 | 0.012 |

TABLE II

The molar proportions between Mg and Ti and between DOP and Ti

| Example | Mg | Ti | DOP |
|---|---|---|---|
| 5 | 1.7 | 1 | 0.86 |
| 6 | 7.2 | 1 | 1.28 |
| 7 | 18.9 | 1 | 1.87 |

TABLE 12

The calculated Cl content in the catalysts compared to the measured amounts

| Example | Calculated Cl w-% | Found Cl w-% |
|---|---|---|
| 5 | 36.8 | 36.4 |
| 6 | 42.2 | 45.0 |
| 7 | 43.3 | 44.5 |

Activity of the Catalysts

Figure 4:
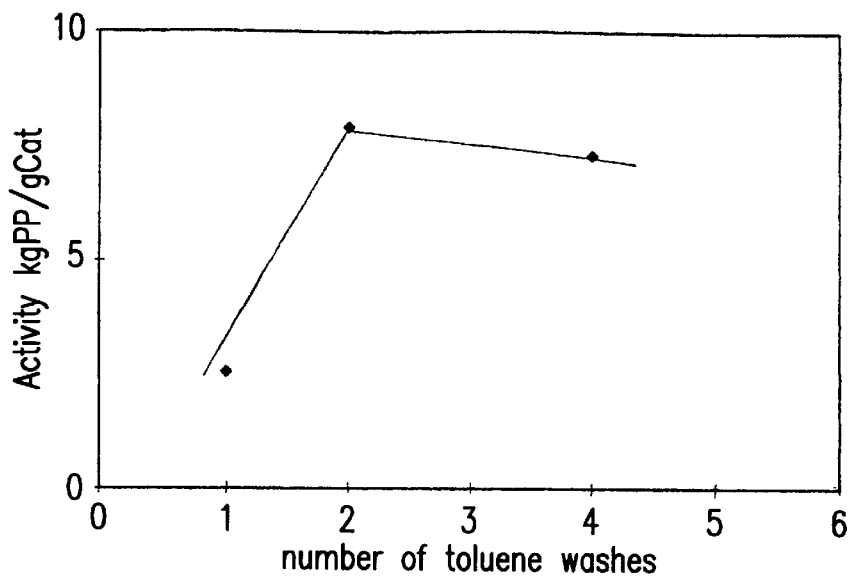
FIGS. 4 and 5 show the correlation between the activity and the number of toluene washes used in the catalyst synthesis.
Figure 5:
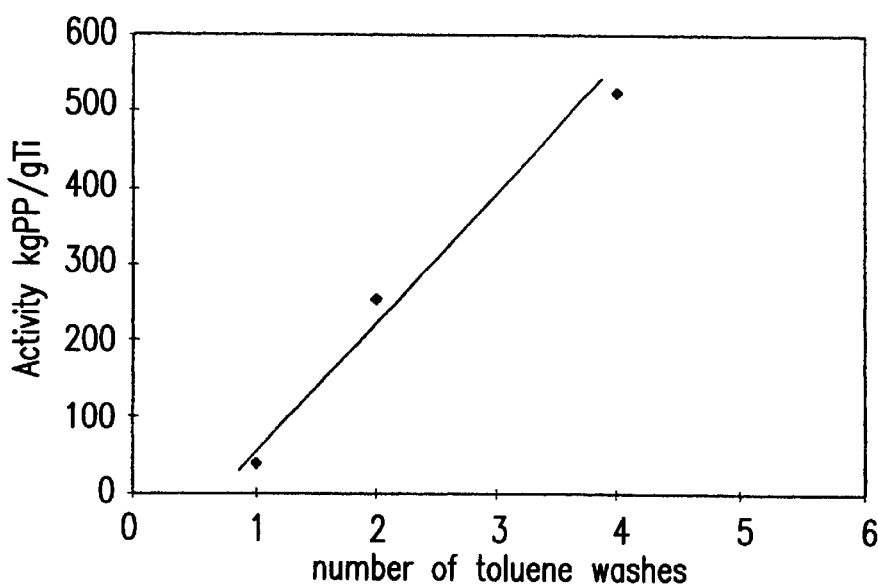

All the catalysts were test polymerized according to the above instructions. The polymerization results are listed in Table 13 in both kg PP/g cat and kg PP/g Ti units. The activities are also shown in FIG. 4 and FIG. 5. Activities of almost 8 kg PP/g cat were reached. Catalysis of the examples 5, 6 and 7 gave good polymerization results, with the highest activity achieved for the catalyst that had been twice washed with toluene. The activities expressed in kg PP/g Ti units showed an linear increase related to the number of toluene washes for the catalysts of examples 5, 6 and 7 (FIG. 5). Activities of over 500 kg PP/g Ti were reached.

Characterization of the Polymers

All the polymers were characterized with respect to their melt flow rate (MFR) and bulk density (BD). All the polymers showed to have a $MFR_2$ between 11–12 g/10 min, indicating a quite good hydrogen response. Bulk densities were between 0.35–0.39 g/ml. The total solubles were between 2 and 3%, being better for the polymers achieved with the catalyst giving higher activity. The results listed in Table 14.

TABLE 13

The polymerization results

| Example | Activity kg PP/g cat | Activity kg PP/g Ti |
|---|---|---|
| 5 | 2.6 | 38 |
| 6 | 7.9 | 254 |
| 7 | 7.3 | 524 |

TABLE 14

The polymer properties

| Example | MFR 2.16 kg, 10 min | TS % | BD g/ml |
|---|---|---|---|
| 5 | 11.0 | 3.1 | 0.360 |
| 6 | 12.4 | 2.1 | 0.350 |
| 7 | 11.0 | 2.1 | 0.390 |

IR Studies of the Catalyst

Figure 6:
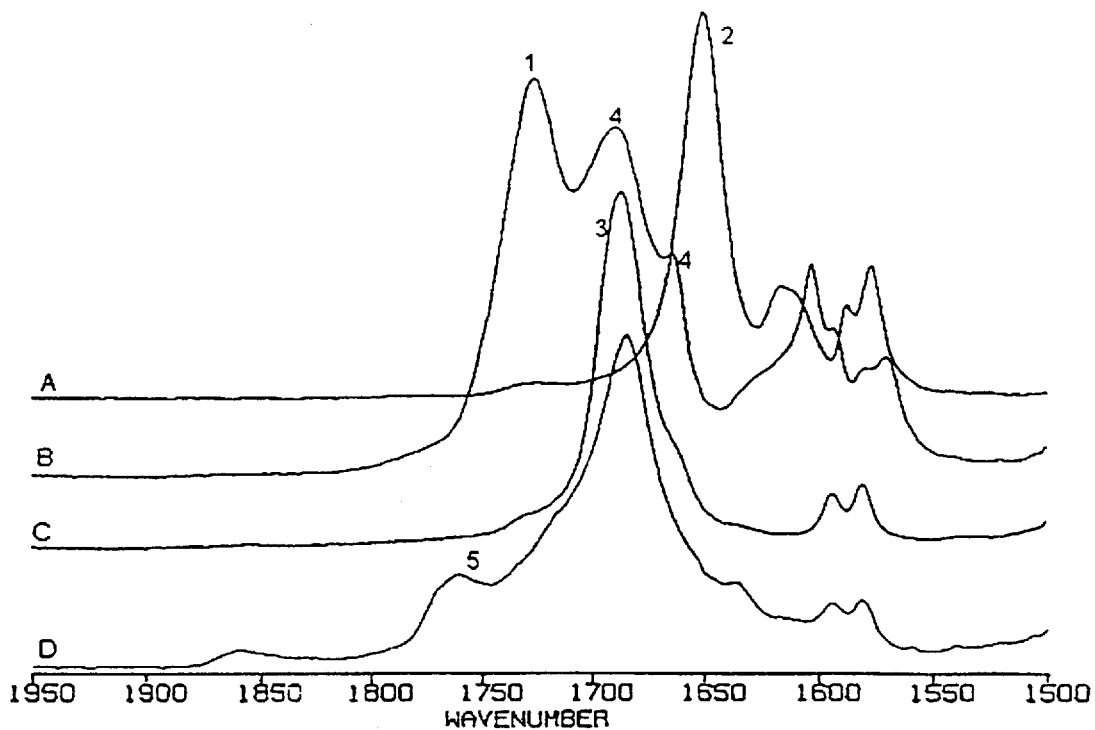
FIG. 6 shows the details of IR spectra in the C=O metal complex region of TiCl$_4$.DUP.
Figure 7:
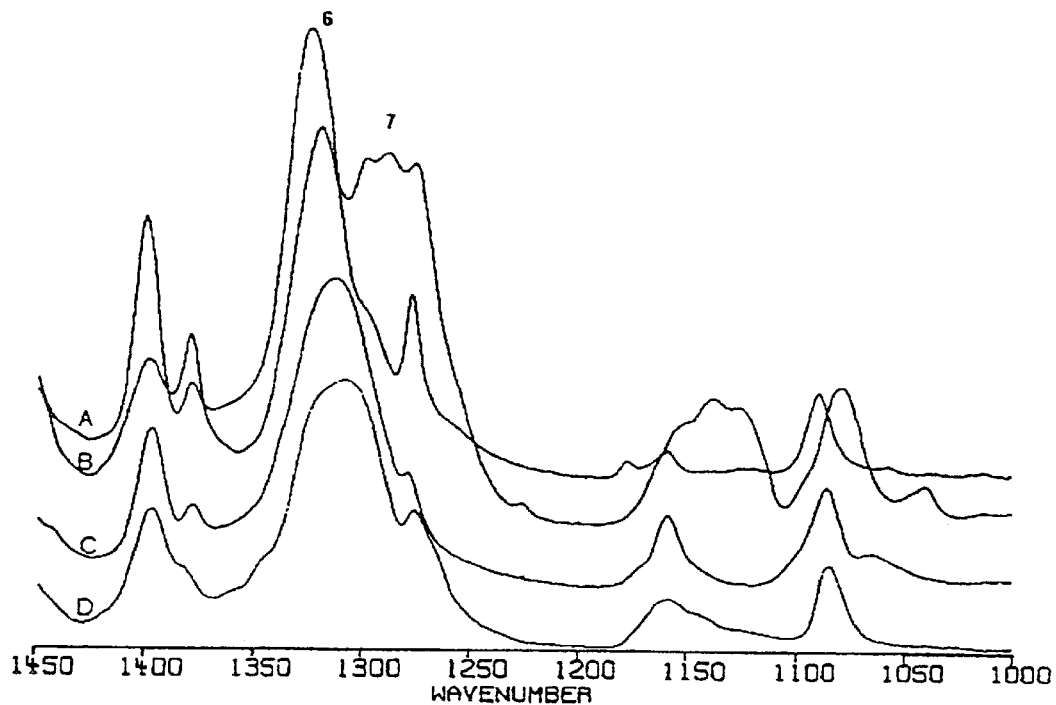
FIG. 7 shows the details of IR spectra in the C=O——— metal complex region of TiCl$_4$.DUP.

IR spectra in the corresponding regions of 1500–1950 $cm^{-1}$ (FIG. 6) and of 1000–1450 $cm^{-1}$ (FIG. 7) were taken from the resulting catalyst of example 6 and compared to an IR spectrum of a typical active catalyst complex coming from a synthesis starting from a $MgCl_2.(EtOH)_3$ support material. The spectra are essentially different, and also different from the IR spectra of the isolated complexes of $TiCl_4/DOP$ and $MgCl_2/DOP$.

X-ray Studies of the Catalysts

As described above, X-ray diffraction patterns were taken from the resulting catalysts and compared to a X-ray pattern from an inactive catalyst complex and a typical active catalyst complex prepared from a $MgCl_2.3EtOH$ support material.

Figure 8:
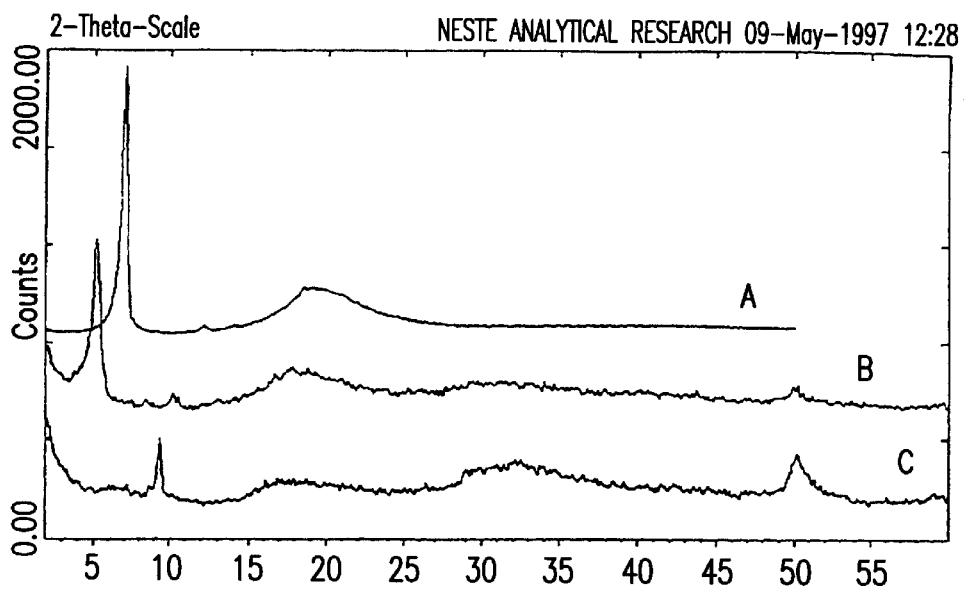
FIG. 8 shows the X-ray patterns of Mg(OR)$_2$ and MgCl$_2$.TiCl$_4$.DOP.

In FIG. 8 are shown the X-ray patterns of $Mg(OR)_2$ (A) $MgCl_2.TiCl_4.DOP$ (B) produced from $MgCl_2.3EtOH$, and of $(MgCl_2)_{1.7}.TiCl_4.DOP$ (C) produced by adding one mol $MgCl_2.DOP$ to 10 moles of $TiCl_4$. In all these cases there was a strong peak located somewhere between 5° and 9° 2Θ. In addition, there seems to be a halo formation between 17° and 23° 2Θ. The strong peak in the left corner of the pattern indicates that large organic groups are separating metal layers at a distance of between 9 and 17 Å, the distance depending on the size of the organic compound (DOP or di-undecyl phthalate DUP). It can thus be stated that the X-ray diffraction patterns for the catalyst complexes originating from the claimed process all show unique features originating from the starting compounds of $Mg(OR)_2$ and $MgCl_2.DOP$. These patterns show almost no sign of amorphous or crystalline $MgCl_2$.

Stoichiometric Comparison

To get a fair picture about how much more stoichiometric the claimed process is compared to a conventional Ziegler-Natta PP catalyst component process, the waste amounts and the volumes of chemicals to be circulated are listed in Table 15. As reference is used a classical Z-N PP catalyst component synthesis with two titanations followed by three heptane washes (as in EP 0 491 566). Example 6 was chosen as the best representative. Here two toluene washes has been used to purify the catalyst. As can be seen from the list, the most essential difference between these two synthesis routes is the lack of the titanium alkoxy trichloride waste material, the $ORTiCl_3$, in this new recipe. The lack of Ti-waste material makes a great difference in easiness in circulating $TiCl_4$. The other significant change is the decrease in the overall use of $TiCl_4$, that has dropped to one fourth of what it has been in the classical recipe. The aliphatic hydrocarbon wash in the classical recipe have been changed to a toluene dito in the new recipe.

TABLE 15

Stoichiometric comparison between a classical Ziegler-Natta PP catalyst synthesis and the claimed (example 6) catalyst synthesis. The figures refer to mol/mol Mg.

| Species | Classical Z-N PP cat synthesis | Example 6 |
|---|---|---|
| $Cl_3$ TiOR waste to be neutralized | 3 | 0 |
| $TiCl_4$ to be circulated | 40 | 10 |
| Donor in excess | 0.1 | 0.8 |
| Hydrocarbon to be circulated | 40 | 7 |
| Toluene to be circulated | 0 | 60 |

EXAMPLE 8

Second Main Embodiment

EXAMPLES 9 AND 10

Third Main Embodiment

The following reagents are used; $MgCl_2$ or $MgR_2$, 2-ethyl-hexanol (EHA), phthaloyl dichloride (PDC) and $TiCl_4$ and they are added in the molecular proportion of 1:2:1:1. In the first synthesis (example 8), the Mg-alkyl is reacted with the alcohol, then the phthaloyl chloride (PDC) is added and finally the $TiCl_4$ is added. In the next two syntheses (examples 9 and 10), the Mg-alkyl is replaced by $MgCl_2$. Either the $TiCl_4$ or the phthaloyl chloride is added in the next step, followed by the last reagent. The synthesis set-ups are is listed in Table 16.

TABLE 16

Addition order of the reaction components in the catalyst synthesis

| Reaction component/Example | 8 | 9 | 10 |
|---|---|---|---|
| $MgR_2$ | 1 | | |
| $MgCl_2$ | | 1 | 1 |
| R'OH | 2 | 2 | 2 |
| PDC | 3 | 3 | 4 |
| $TiCl_4$ | 4 | 4 | 3 |

Preparation of the Complexes

The same volumes of reagents have been used in all the experiments regardless in which order they have been added. Thus 22.22 mmol (25.10 ml, 18.3 g) of a 20% heptane solution of butyl-octyl-Mg (BOMAG) was added in experiment (8) and 22.60 mmol (2.15 g) of $MgCl_2$ was added in experiment (9) and (10). To this, 45.19 mmol (7.10 ml, 5.92 g) of 2-ethyl-1-hexanol EHA was added. The $TiCl_4$ mol amount added was equal to the mol amount of $MgCl_2$ being 22.60 mmol (2.48 ml, 4.29 g) and also equal to the mol amount of PDC added, which was 22.60 mmol (3.26 ml, 4.59 g). The addition orders of the reaction components in each catalyst synthesis are listed in Table 16. All the complexes were washed three times with a 100 ml portion of heptane at 90° C. for 15 min and last with a 100 ml portion of pentane at room temperature. Finally the catalysts were dried under a stream of nitrogen.

Characterization of the Catalysts

All the catalysts were characterized with respect to their chemical composition by measuring their Mg, Ti, Cl and di-octyl-phthalate (DOP) content. The Ti and Mg containing catalyst samples were dissolved in a mixture of nitric and hydrofluoric acid and the metals were measured by flame atomic absorption with a nitrous oxide/acetylene flame. Chloride was determined after dissolution in dilute sulphuric acid by potentiometric titration with a standard silver nitrate solution.

The determination of the phthalic esters and the phthalic anhydride were done by first dissolving the sample in acetone. The dissolution was improved by keeping the acetone slurry in an ultra-sound bath for 5 min. After this the samples were filtered and run by solution chromatography. As eluent a solution consisting of water and acetonitrile in a proportion of 4/96 was used. The eluent flow rate was 1.5 ml/min. A photo diode array was used as detector. Each component, was identified by comparing its retention time and UV spectra with those of standard components. To further characterize the complexes, IR spectra and X-ray diffraction patterns were taken of them.

Bulk Polymerization

The polymerization was carried out as before. See page 18.

Results

Chemical Composition of the Catalysts

As stated in the experimental section, the catalysts were characterized with respect to their chemical composition. In Table 17 the chemical composition of the catalysts with respect to the Mg, Ti, di(2-ethyl-1-hexyl)phthalate (DOP), 2-ethyl-1-hexyl alcohol (EHA) and phthalic anhydride PA contents are listed in w-% units and in Table 18 the same species are listed in mol-% units and last, in Table 19 the molar composition between Mg, Ti and DOP are listed. The examples 8 and 10 are represented by two catalysts, 8a and 8b, as well as 10a and 10b, respectively. The chlorine contents are listed in Table 20.

TABLE 17

The Mg, Ti, DOP, EHA and PA contents of the catalysts in w-% units

| Example | Mg w-% | Ti w-% | DOP w-% | EHA w-% | PA w-% |
|---|---|---|---|---|---|
| 8a | 3.6 | 5.6 | 35.6 | 6.8 | 4.16 |
| 8b | 9.9 | 3.5 | 34.0 | — | — |
| 9 | 3.9 | 7.0 | 35.7 | 5.3 | 1.27 |
| 10a | 4.5 | 7.0 | 43.6 | 5.15 | 1.6 |
| 10b | 11.1 | 3.7 | 33.0 | 1.00 | 0.3 |

TABLE 18

The Mg, Ti, DOP, EHA and PA contents of the catalysts in mol-% units

| Example | Mg mol-% | Ti mol-% | DOP mol-% | EHA mol-% | PA mol-% |
|---|---|---|---|---|---|
| 8a | 0.148 | 0.117 | 0.091 | 0.052 | 0.028 |
| 8b | 0.407 | 0.073 | 0.087 | — | — |
| 9 | 0.161 | 0.146 | 0.091 | 0.041 | 0.009 |
| 10a | 0.185 | 0.146 | 0.112 | 0.040 | 0.011 |
| 10b | 0.457 | 0.077 | 0.085 | 0.008 | 0.002 |

TABLE 19

Comparison between the molar amounts of Mg, Ti and DOP

| Example | Mg/Ti | Ti | DOP/Ti |
|---|---|---|---|
| 8a | 1.3 | 1 | 0.8 |
| 8b | 5.6 | 1 | 1.2 |
| 19 | 1.1 | 1 | 0.6 |
| 10a | 1.3 | 1 | 0.8 |
| 10b | 5.6 | 1 | 1.1 |

TABLE 20

The calculated amounts of Cl in the catalysts compared to the amounts found

| Example | Calculated w-% | Found w-% |
|---|---|---|
| 8a | 27.1 | 26.0 |
| 8b | 39 | — |
| 9 | 32.1 | 30.9 |
| 10a | 33.5 | 32.4 |
| 10b | 43.4 | 44.0 |

The IR Results

Figure 9:
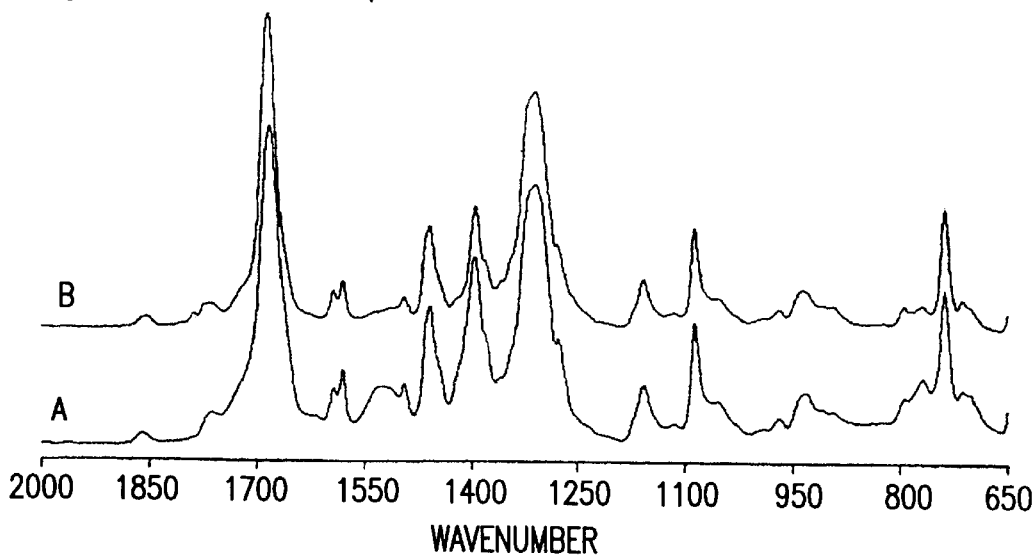

In FIG. 9 is shown the IR spectra of the catalyst components of examples 9 and 10a. There were clear indications of the presence of phthalic anhydride in the catalyst that has been prepared from $MgR_2$ (example 8a). The phtalic anhydride was almost totally missing from the samples that had been prepared out of $MgCl_2$ (examples, 9 and 10a). These results confirm the results of the chemical analysis. The IR spectrum (not shown) for the toluene washed example 10b catalyst showed no traces of phthalic anhydride but to the left of the C=O————Ti peak a shoulder had appeared indicating the presens of some free carboxylic acid group (—COOH).

The X-ray Diffraction Patterns

Figure 10:
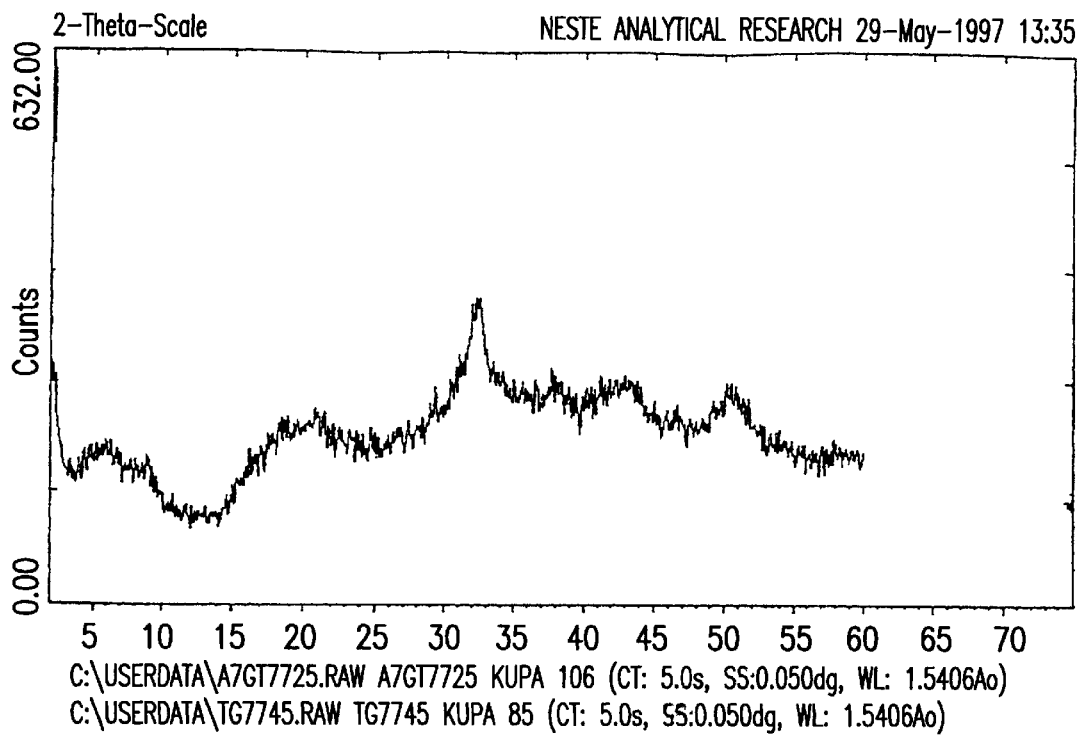
Figure 11:
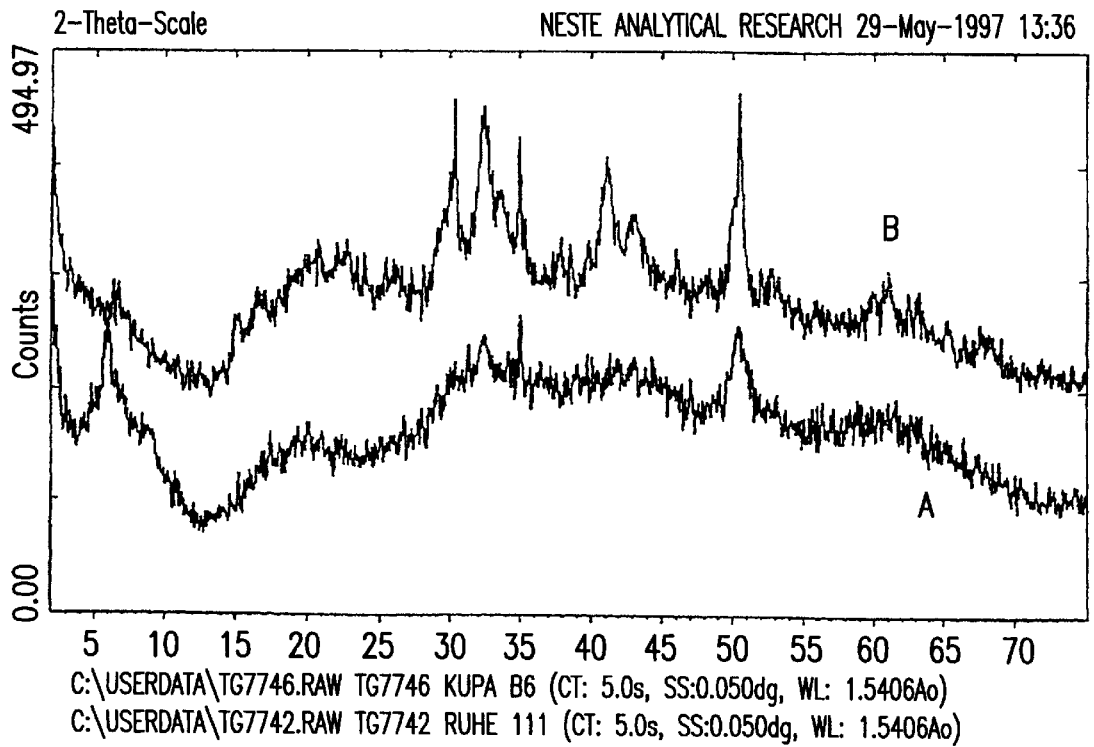
Figure 12:
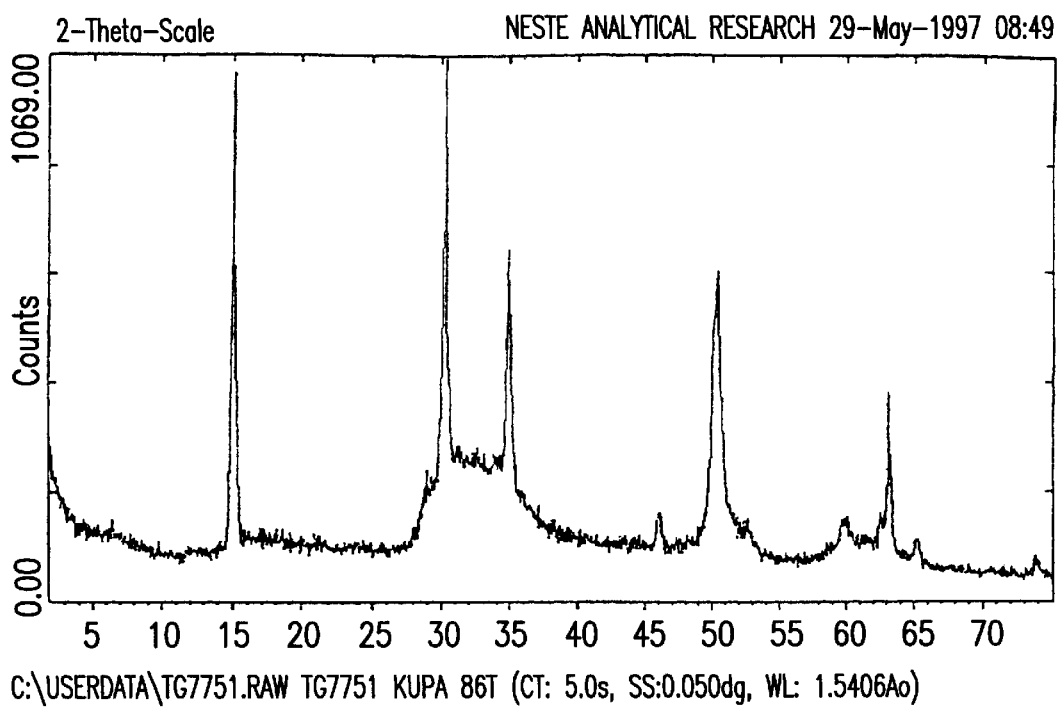
FIG. 12 shows the X-ray pattern of Example 10b.

In FIGS. 10, 11 and 12, the X-ray diffraction patterns for the catalysts are shown. The results show that the addition of $TiCl_4$ before PDC gives a more crystalline material. This can be seen in FIG. 11. Example 9 is still showing the organic separation peak at 7° 2Θ and the halo between 18° and 22° 2Θ but only a slight remain thereof can be seen of the halo in the spectrum of example 10a. In all patterns there seems to be an additional peak at about 32°–33° 2Θ. This peak is not connected to crystalline $MgCl_2$. Some unreacted $MgCl_2$ seems to be present in the catalyst component of example 10a which is starting to dominate when the catalyst is washed with toluene (FIG. 12).

Polymerization Results

Figure 13:
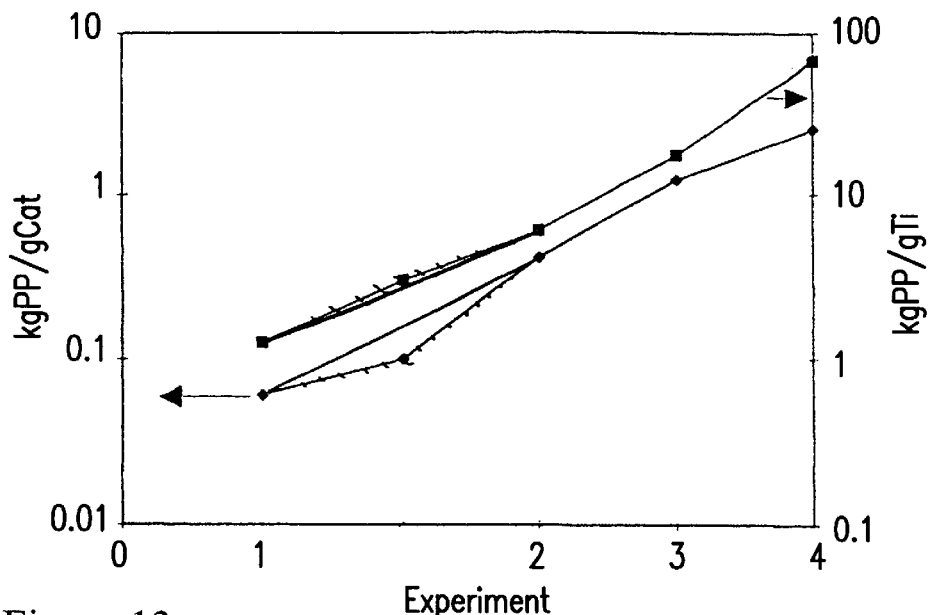
FIG. 13 shows the activities of the catalysts coming from experiments 8b–10b.

All but one (example 8a) of the catalysts were test polymerized according to the descriptions in the experimental section. The polymerization results both in kg PP/g cat units and in kg PP/g Ti units are listed in Table 21. In FIG. 13 the results are shown graphically. There was an almost logaritmic linear increase in the activities. As a whole it can be said that:

1. Addition of $TiCl_4$ before PDC gives better activity (compare examples 9 and 10).
2. Starting from $MgCl_2$ instead of from $MgR_2$ gives higher activity (compare example 8 with examples 9 and 10).
3. Toluene wash improves activity (compare examples 10a and 10b).

TABLE 21

The polymerization results

| Example | Activity kg PP/g cat. | Activity kg PP/g Ti |
|---|---|---|
| 8b | 0.06 | 1.3 |
| 9 | 0.4 | 6.0 |
| 10a | 1.2 | 18 |
| 10b | 2.5 | 67 |

What is claimed is:

1. A process for the preparation of an olefin polymerization catalyst component containing magnesium, titanium, halogen and an electron donor comprising the steps of:
   (i) reacting a titaniumless magnesium compound (a) containing an alkoxy moiety, which titaniumless magnesium compound is selected from the group consisting of a compound or complex containing halogen and alkoxide linked to magnesium, a complex containing a magnesium dihalide and an alcohol, and a non-complex magnesium dialkoxide, with a halogen compound (b) being capable of forming the electron donor by replacement of its halogen by said alkoxy moiety, to give an intermediate (ab), and
   (ii) reacting said intermediate (ab) with a titanium halide (c), or
   (i)' reacting a titaniumless magnesium compound (a) containing an alkoxy moiety, which titaniumless magnesium compound is selected from the group consisting of a compound or complex containing halogen and alkoxide linked to magnesium, and a complex containing a magnesium dihalide and an alcohol, with a titanium halide (c) to give an intermediate (ac), and
   (ii)' reacting said intermediate (ac) with a halogen compound (b) being capable of forming the electron donor by replacement of its halogen by said alkoxy moiety,
   wherein (i), (ii), (i)' and (ii)' are carried out in solution;
   wherein said complex containing halogen and alkoxide linked to magnesium is selected from the group consisting of $MgCl_2[Mg(OR)_2]_t$, wherein R is a $C_1$–$C_{20}$ alkyl or a $C_7$–$C_{27}$ aralkyl, and t is 1–6; and
   $Mg_pX_q(OR)_{2p-q}$, wherein X is a halogen, R is an alkyl group having from 1 to 20 carbon atoms, p is from 2 to 20 and Q<0.66p with the proviso that for steps (i)' and (ii)' q>0;
   wherein said complex containing a magnesium dihalide and an alcohol is
   $MgCl_2 \cdot (ROH)_m$, wherein R is a $C_1$–$C_{20}$ alkyl or a $C_7$–$C_{27}$ aralkyl, and m is 1–6;
   wherein said compound containing halogen and alkoxide linked to magnesium is
   $MgXOR \cdot nR'OH$, wherein X is a halogen, R and R' are a $C_1$–$C_{12}$ hydrocarbyl and n is 0–6; and
   wherein the halogen compound (b) is an organic acid halide.

2. A process according to claim 1, wherein the reaction product of step (ii) or step (ii)' is recovered by precipitation.

3. A process according to claim 1, wherein said compounds (a), (b) and (c) are contacted in stoichiometric amounts, or alternatively, that a stoichiometric excess with respect to said titaniumless magnesium compound (a), of said titanium halide (c) is used.

4. A process according to claim 1, wherein said magnesium dihalide is magnesium dichloride $MgCl_2$.

5. A process according to claim 1, wherein said halogen compound (b) is an organic acid halide, whereby the electron donors formed from therefrom are, correspondingly, an organic acid ester.

6. A process according to claim 1, wherein said titanium halide (c) is a titanium tetrahalide.

7. A process according to claim 1, comprising the steps of:
   (i) reacting said compound or complex containing halogen and alkoxide linked to magnesium as said titaniumless magnesium compound (a) with said halogen compound (b) to give an intermediate (ab) and
   (ii) reacting said intermediate (ab) with said titanium halide (c), or:
   (i)' reacting said compound or complex containing halogen and alkoxide linked to magnesium as said titaniumless magnesium compound (a) with said titanium halide (c) to give an intermediate (ac) and
   (ii)' reacting said intermediate (ac) with said halogen compound (b).

8. A process according to claim 7, wherein said compound or complex containing halogen and alkoxide linked to magnesium as said titaniumless magnesium compound (a) is a complex of a magnesium dihalide and a magnesium dialkoxide.

9. A process according to claim 8, comprising the steps of
   (i)' reacting a magnesium dichloride-dimagnesium dialkoxide complex $MgCl_2[Mg(OR)_2]_2$ (a) wherein R is a $C_1$–$C_{20}$ alkyl or a $C_7$–$C_{27}$ aralkyl with said titanium halide (c), which is said titanium tetrachloride $TiCl_4$, to give an intermediate (ac) and
   (ii)' reacting said intermediate (ac) with said halogen compound (b), which is said phthalic acid dichloride $Ph(COCl)_2$, wherein Ph is o-phenylene.

10. A process according to claim 1, comprising the steps of:
    (i) reacting said titaniumless magnesium compound (a) which is selected from said complex of said magnesium dihalide and said alcohol, and said non-complex magnesium dialkoxide, with said halogen compound (b) to give an intermediate (ab) which is a complex of said magnesium dihalide or said non-complex magnesium dialkoxide and said electron donor and
    (ii) reacting said intermediate (ab) which is a complex of said magnesium dihalide or said non-complex magnesium dialkoxide and said electron donor with said titanium halide (c).

11. A process according to claim 10, wherein independently, said complex of said magnesium dihalide and said alcohol is a magnesium dichloride-alcohol complex $MgCl_2 \cdot (ROH)_m$, wherein R is a $C_1$–$C_{20}$ alkyl or a $C_7$–$C_{27}$ aralkyl, and m is 1–6, and said non-complex magnesium alkoxide is a magnesium dialkoxide $Mg(OR)_2$, wherein R is a $C_1$–$C_{20}$ alkyl or a $C_7$–$C_{27}$ aralkyl.

12. A process according claim 1, comprising the steps of:
    (i)' reacting said titaniumless magnesium compound (a), which is said complex of said magnesium dihalide and said alcohol, with said titanium halide (c) to give an intermediate (ac) and
    (ii)' reacting said intermediate with said halogen compound (b).

13. A process according to claim 12, wherein said complex of said magnesium dihalide and said alcohol compound is a magnesium dichloride-alcohol complex $MgCl_2 \cdot (ROH)_m$, wherein R is a $C_1$–$C_{20}$ alkyl or a $C_7$–$C_{27}$ aralkyl, and m is 1–6.

14. A process according to claim 13, comprising the steps of
(i)' reacting said titaniumless magnesium compound (a), which is said magnesium dichloride-alcohol complex $MgCl_2 \cdot (ROH)_m$, wherein R is a $C_1$–$C_{20}$ alkyl or a $C_7$–$C_{27}$ aralkyl, and m is 1–6, with said titanium dihalide (c), which is said titanium tetrachloride $TiCl_4$, to give an intermediate (ac) and
(ii)' reacting said intermediate (ac) with said halogen compound (b), which is said phthalic acid dichloride $Ph(COCl)_2$, wherein Ph is o-phenylene.

15. A process according to claim 7, wherein that in step (ii) said intermediate (ab) is added, drop-by-drop, to said titanium halide (c), which is in liquid form and 75–150° C.

16. A process according to claim 7, further comprising
(iii) the obtained reaction product of step (ii) or (ii)' is further treated with said titanium halide (c) and washed with an aromatic hydrocarbon or an organic liquid having the same solubility parameter as said aromatic hydrocarbons.

17. A catalyst component comprising magnesium, titanium, a halogen and an electron donor, characterized in that it has been prepared by the process described in claim 1.

18. The catalyst component according to claim 17, comprising an isolated complex of a magnesium dihalide, and electron donor obtained by replacing the halogen of a halogen compound by an alkoxy group, and a titanium halide.

19. The catalyst component according to claim 17, wherein said complex has an X-ray pattern comprising a crystal height indicating peak between 16° and 18° 2θ (Siemens D500 instrument, CuKα radiation wavelength 1.541 Å, effect 40 kV and 35 mA).

20. The catalyst component according to claim 17, 18 or 19, characterized in that said complex is prepared by contacting stoichiometric amounts of said components (a), (b) and (c).

21. The catalyst component according to claim 18, wherein said complex has an X-ray diffraction pattern comprising a peak between 5° and 10° 2θ (Siemens D500 instrument, CuKα radiation wavelength 1.541 Å, effect 40 kV and 35 mA).

22. The catalyst component according to claim 18, wherein no $TiCl_3OR$ waste material is produced in the catalyst synthesis.

23. A method of polymerizing α-olefins comprising contacting olefins with the catalyst compound of claim 17.

24. The method of claim 23, wherein, said catalyst component comprises an organometal compound of a metal belonging to Group 1, 2 or 13 (IUPAC 1990) of the Periodic Table.

25. The process according to claim 3, wherein a 5–20 fold stoichiometric excess with respect to said titaniumless magnesium compound (a) of said titanium halide (c), is used.

26. The process according to claim 5, wherein said organic acid halide is phthalic acid dichloride, whereby the electron donor formed is a phthalic acid diester $Ph(COOR)_2$, and wherein said Ph is o-phenylene and R is a $C_1$–$C_{20}$ alkyl or a $C_7$–$C_{27}$ aralkyl.

27. The process according to claim 26, wherein said phthalic acid diester is a di-$C_6$–$C_{26}$ alkyl phthalate.

28. The process according to claim 27, wherein said di-$C_6$–$C_{26}$ alkyl phthalate is dioctyl phthalate.

29. The process according to claim 6, wherein said titanium tetrahalide is titanium tetrachloride ($TiCl_4$).

30. The process according to claim 8, wherein said complex of a magnesium dihalide and a magnesium dialkoxide is a magnesium dichloride-dimagnesium dialkoxide complex $MgCl_2[Mg(OR)_2]_2$, and wherein said R is a $C_1$–$C_{20}$ alkyl or a $C_7$–$C_{27}$ aralkyl.

31. The process according to claim 30, wherein said R is a $C_6$–$C_{16}$ alkyl.

32. The process according to claim 31, wherein said complex has been prepared by reacting magnesium dichloride ($MgCl_2$) with an alcohol (ROH) to give an intermediate and reacting the intermediate with a dialkyl magnesium $MgR'''_2$, and wherein said R''' is defined as for R.

33. The process according to claim 9, wherein said R is a $C_6$–$C_{16}$ alkyl.

34. The process according to claim 11, wherein said magnesium alkoxide has been prepared by reacting a magnesium dialkyl and an alcohol (ROH).

35. The process according to claim 11, wherein said R is a $C_6$–$C_{16}$ alkyl.

36. The process according to claim 12, wherein said R is a $C_6$–$C_{16}$ alkyl and said m is 1–6.

37. The process according to claim 14, wherein said R is a $C_6$–$C_{16}$ alkyl.

38. The process according to claim 16, wherein said reaction product is repeatedly washed with an aromatic hydrocarbon or an organic liquid having the same solubility parameter as said aromatic hydrocarbon.

39. The process according to claim 38, wherein said hydrocarbon is toluene.

40. The catalyst component according to claim 18, wherein said magnesium dihalide is magnesium dichloride.

41. The catalyst component according to claim 18, wherein said electron donor is a phthalic acid diester.

42. The catalyst component according to claim 18, wherein said titanium halide is titanium tetrachloride.

43. The process according to claim 23, said α-olefin is propene.

44. The process according to claim 24, wherein said organometal compound is an alkyl aluminum compound.

* * * * *